United States Patent
Poindexter et al.

(10) Patent No.: US 6,479,482 B2
(45) Date of Patent: Nov. 12, 2002

(54) ALKYLAMINE DERIVATIVES OF DIHYDROPYRIDINE NPY ANTAGONISTS

(75) Inventors: Graham S. Poindexter, Old Saybrook, CT (US); Marc Bruce, Wallingford, CT (US); Sing-Yuen Sit, Meriden, CT (US); Scott W. Martin, Middletown, CT (US)

(73) Assignee: Bristol-Myers Squibb Company, Princeton, NJ (US)

( * ) Notice: Subject to any disclaimer, the term of this patent is extended or adjusted under 35 U.S.C. 154(b) by 0 days.

(21) Appl. No.: 09/852,983

(22) Filed: May 10, 2001

(65) Prior Publication Data

US 2002/0019384 A1 Feb. 14, 2002

Related U.S. Application Data

(60) Provisional application No. 60/202,901, filed on May 10, 2000.

(51) Int. Cl.$^7$ ............... C07D 417/14; A61K 31/541
(52) U.S. Cl. ............... 514/227.8; 514/318; 544/60; 546/194
(58) Field of Search ............... 546/194; 514/318, 514/227.8; 544/60

(56) References Cited

U.S. PATENT DOCUMENTS

| | | | |
|---|---|---|---|
| 4,829,076 A | 5/1989 | Szilagyi et al. | |
| 5,554,621 A | 9/1996 | Poindexter et al. | |
| 5,635,503 A | 6/1997 | Poindexter et al. | |
| 5,668,151 A | 9/1997 | Poindexter et al. | |
| 6,001,836 A | 12/1999 | Poindexter et al. | |

OTHER PUBLICATIONS

Chaurasia, et al., "Nonpeptide Peptidomimetic Antagonists of the Neuropeptide Y Receptor: Benextramine Analogs with Selectivity for the Peripheral Y2 Receptor," J. Med. Chem., 1994, 37, 2242–2248.

Rudolf, et al., "The First Highly Potent and Selective Non–peptide Neuropeptide Y Y1 Receptor Antagonist: BIBP3226," European Journal of Pharmacology, 271, 1994, R11–R13.

Serradeil–Le Gal, et al., "SR120819A, An Orally–Active and Selective Neuropeptide Y Y1 Receptor Anatagonist," FEBS Letters, 362, 1995, 192–196.

*Primary Examiner*—Jane Fan
(74) *Attorney, Agent, or Firm*—Richard P. Ryan

(57) ABSTRACT

A series of non-peptidergic antagonists of NPY have been synthesized and are comprises of amino and piperazine derivatives of 4-phenyl-1,4-dihydropyridines of Formula 1.

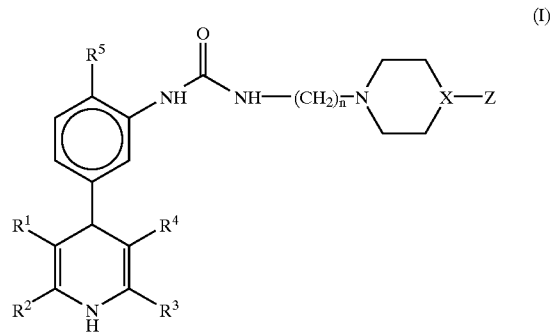

(I)

where X is CH or N

As antagonists of NPY-induced behavior, these compounds are expected to act as effective anorexiant agents in promoting weight loss and treating eating disorders.

9 Claims, No Drawings

ALKYLAMINE DERIVATIVES OF DIHYDROPYRIDINE NPY ANTAGONISTS

CROSS REFERENCE TO RELATED APPLICATION

This non-provisional application claims priority from provisional application U.S. Ser. No. 60/202,901 filed May 10, 2000.

FIELD OF THE INVENTION

The present invention is directed to heterocyclic compounds comprising 4-phenyl-1,4-dihydropyridines having alkyl amine moieties connected to the 3-position of the phenyl ring. More particularly, the invention is directed to NPY antagonist of alkylamine derivatives of 4-phenyl-1,4-dihydropyridine.

BACKGROUND OF THE INVENTION

Neuropeptide Y (NPY) is a 36 amino acid peptide first isolated in 1982 from porcine brain. The peptide is a member of a larger peptide family which also includes peptide YY (PYY), pancreatic peptide (PP), and the non-mammalian fish pancreatic peptide Y (PY). Neuropeptide Y is very highly conserved in a variety of animal, reptile and fish species. It is found in many central and peripheral sympathetic neutrons and is the most abundant peptide observed in the mammalian brain. In the brain, NPY is found most abundantly in limbic regions. The peptide has been found to elicit a number of physiological responses including appetite stimulation, anxiolysis, hypertension, and the regulation of coronary tone.

Structure-activity studies with a variety of peptide analogs (fragments, alanine replacements, point mutations, and internal deletion/cyclized derivatives) suggest a number of receptor subtypes exist for NPY. These currently include the $Y_1$, $Y_2$, $Y_3$, and the $Y_{1-like}$ or $Y_4$ subtypes.

Although a number of specific peptidic antagonists have been identified for most of the subtypes, few selective non-peptidic antagonists have been reported to date. The heterocyclic guanidine derivative He 90481 (4) was found to be a weak but competitive antagonist of NPY-induced $Ca^{++}$ entry in HEL cells ($pA_2$=4.43). The compound was also found to have $\alpha_2$-adrenergic and histaminergic activity at this dose range. D-Myo-inositol-1,2,6-triphosphate was reported to be a potent but non-competitive antagonist to NPY-induced contractions in guinea pig basilar artery. Similarly, the benextramine-like bisguanidines were reported to displace $^3$H-NPY in rat brain ($IC_{50}$, 19 and 18.4 $\mu$M) and to display functional antagonism in rat femoral artery. The bisguanidine was shown to be functionally selective for the $Y_2$ receptor since it antagonized the effect of the $NPY_2$ agonist $NPY_{13-36}$ but had no effect on the vasoconstrictive activity of the $NPY_1$ agonist [$Leu^{31}$, $PrO^{34}$] NPY as disclosed in *J. Med. Chem.*, 1994, 37, 2242–48, C. Chauraisia, et al.

Compound BIBP 3226, as reported in K. Rudolf, et al., *Eur. J. Pharmacol.*, 1994, 271, R11–R13, displaces I-125 Bolton-Hunter labeled NPY in human neuroblastoma cells (SK-N-MC). BIBP antagonized the NPY-induced increase in intracellular $Ca^{++}$ in SK-N-MC cells as well as antagonizing the NPY-induced pressor response in pithed rat experiments.

In addition to displacing I-125 labeled NPY and PYY in human neuroblastoma cells, compound SR 120819A, as reported in C. Serradeil-LeGal, et al., *FEBS Lett.*, 1995, 362, 192-A6, also antagonized NPY-related increases in diastolic blood pressure in an anesthetized guinea pig model.

Over the past two decades, extensive work has been conducted relating to the 4-aryl-1,4-dihydropyridine class of compounds. Syntheses of compounds in this category have been driven by their pharmacological actions involving calcium channels rendering them useful for treating cardiovascular disorders such as ischemia and hypertension.

Numerous prior patents and publications disclose various dihydropyridine derivatives. One example is U.S. Pat. No. 4,829,076 to Szilagyi, et al. disclosing compounds of formula (1) as calcium antagonists for treating hypertension.

(1)

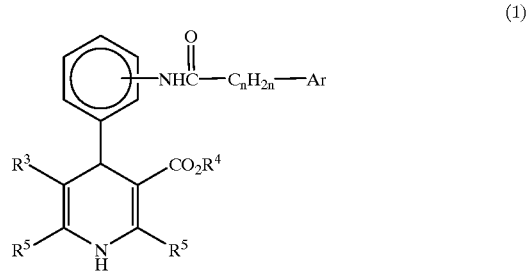

U.S. Pat. No. 5,635,503 to Poindexter, et al. discloses 4-(3-substituted-phenyl)-1,4-dihydropyridine derivatives having NPY antagonist properties. These derivatives conform to structural formula (2).

(2)

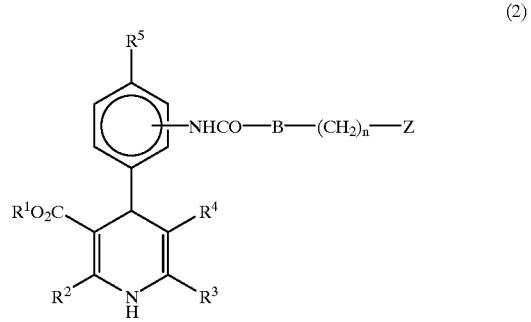

In (2), B is either a covalent bond or the group —NH—. The symbol Z denotes hetaryl moieties, examples being homopiperazinyl or piperazine.

U.S. Pat. No. 5,554,621 discloses related derivatives where Z is a fused ring or a spiro-fused nitrogen heterocycle. U.S. Pat. No. 5,668,151 also discloses related derivatives where Z is a piperidinyl or tetrahydropyridinyl.

U.S. Pat. No. 6,001,836 to Poindexter, et al. discloses cyanoguanidine derivatives (3) of the 4-(3-substituted-phenyl)-1,4-dihydropyridines having NPY antagonist properties.

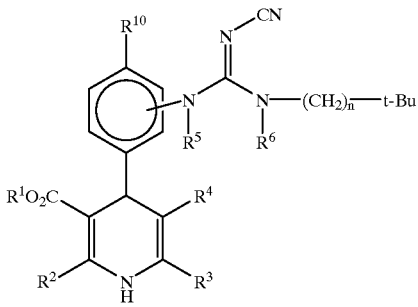

(3)

The above-noted compounds have been shown to possess antagonist activity. However, there is a continuing need for dihydropyridine derivatives having improved NPY antagonist activity.

SUMMARY OF THE INVENTION

The present invention is directed to novel dihydropyridine derivatives having NPY antagonist activity. More particularly, the invention is directed to amine derivatives of dihydropyridines.

Accordingly, a primary aspect of the invention is to provide alkylamine derivatives of dihydropyridines having a lower molecular weight than many prior NPY antagonists.

Another aspect of the invention is to provide a alkylamine derivative of dihydropyridine having greater water solubility compared to prior NPY antagonists.

The compounds of the invention are effective in promoting weight loss and treating disorders in a mammal by administering to the mammal a anorexiant effective dose of an active compound of the invention.

A further aspect of the invention is to provide a method of treating clinical disorders amenable to alleviation by eliciting an NPY $Y_1$ response by administering to a patient an effective amount of a compound of the invention.

Another aspect of the invention is to provide a pharmaceutical composition for use in promoting weight loss and treating eating disorders, where the composition comprises an anorexiant effective amount of an active compound of the invention and a pharmaceutically acceptable carrier.

The compounds of the invention have the Formula I and its pharmaceutically acceptable acid addition salts or hydrates thereof

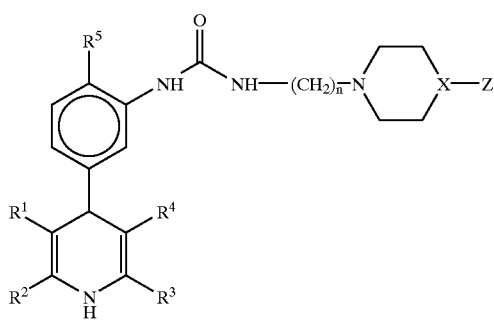

(I)

wherein

X is CH or N;

$R^1$ and $R^4$ are independently selected from lower alkyl and $CO_2R^6$ where $R^6$ is lower alkyl;

$R^2$ and $R^3$ are independently selected from lower alkyl;

$R^5$ is hydrogen or halogen;

n is an integer selected from 2 to 5;

Z is a hydrogen, lower alkyl or

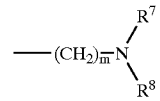

with the proviso that when X is N, Z is a lower alkyl, m is zero or the integer 1 or 2; and $R^7$ and $R^8$ are independently selected from the group consisting of hydrogen, alkyl, cycloalkyl, alkylene, phenyl, alkylamino, heterocyclic alkyl, methoxy, cyanoalkyl, lower alkanol, naphthyl, furfuryl, tetrahydrofurfuryl, methylthioalkyl, thiophene, lower alkyl ethers, esters, acetamides and carbamates, or $R^7$ and $R^8$ are taken together to form —$(CH_2CH_2)_2$—S=$O_m$.

These and other aspects of the invention will become apparent to one skilled in the art as described in the following detailed description.

DETAILED DESCRIPTION OF THE INVENTION

The present invention is directed to novel compounds having NPY $Y_1$ antagonist activity and pharmaceutical compositions containing the novel compounds. The invention is further directed to a method of treating clinical disorders, such as eating disorders, using the novel compounds of the invention.

The compounds of the invention have the Formula I

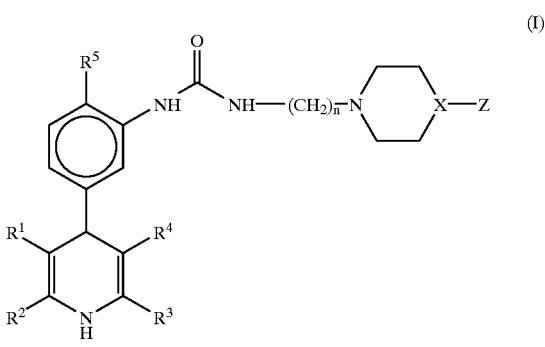

(I)

The compounds within the preview of the invention include the pharmaceutically acceptable acid addition salts and/or hydrates of the compounds of Formula I.

In the Formula I, X, $R^1$–$R^5$, and Z have the following meanings:

X is CH or N.

$R^1$ and $R^4$ are independently selected from lower alkyl and $CO_2R^6$ where $R^6$ is lower alkyl. A preferred lower alkyl for $R^1$ and $R^6$ is methyl.

$R^2$ and $R^3$ are independently selected from lower alkyl, with methyl being preferred.

$R^5$ is hydrogen or halogen. The halogen can be F, Cl, Br or I, with the preferred halogen being F.

n is an integer selected from 2 to 5, with 3 being preferred.

Z is a hydrogen, lower alkyl or

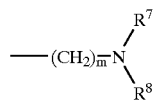

with the proviso that when X is N, Z is a lower alkyl,
m is zero or the integer 1 or 2; and
R⁷ and R⁸ are independently selected from the group consisting of hydrogen, alkyl, cycloalkyl, alkylene, phenyl, alkylamino, heterocyclic alkyl, methoxy, cyanoalkyl, lower alkanol, naphthyl, furfuryl, tetrahydrofurfuryl, methylthioalkyl, thiophene, lower alkyl ethers, esters, acetamides and carbamates or R⁷ and R⁸ are taken together to form —(CH₂CH₂)₂—S=O$_m$ where m is again selected from 0, 1 or 2.

The term "lower" refers to substituents such as alkyl or alkoxy groups that contain from one to four carbon atoms. Alkenyl groups generally contain two to four carbon atoms. In embodiments of the invention, R¹ is preferably CO₂R⁶ where R⁶ is methyl. R² and R³ are preferably methyl. R⁵ is preferably hydrogen or fluorine. Z is preferably an alkyl amine. In further embodiments, Z is a lower alkyl when R⁵ is fluorine.

The compounds of the present invention can exist as optical isomers and both the racemic mixtures of these isomers as well as the individual optical isomers themselves are within the scope of the present invention. The racemic mixtures can be separated into their individual isomers through well-known techniques such as the separation of the diastereomeric salts formed with optically active acids, followed by conversion back to the optically active bases.

As indicated, the present invention also pertains to the pharmaceutically acceptable non-toxic salts of these basic compounds. Such salts include those derived from organic and inorganic acids such as, without limitation, hydrochloric acid, hydrobromic acid, phosphoric acid, sulfuric acid, methanesulfonic acid, acetic acid, dichloroacetic acid, tartaric acid, lactic acid, succinic acid, citric acid, maleic acid, fumaric acid, sorbic acid, aconitic acid, salicyclic acid, phthalic acid, enanthic acid, and the like.

The compounds of the invention can be produced by various processes that use variations of the Hantzsch synthetic reaction applied to the appropriate starting materials. The Formula I compounds containing urea linkages can be synthesized according to Scheme I. (The Schemes are set forth infra, following the examples.)

The process of Scheme I involves conversion of the aniline intermediate 11 by adding dropwise a solution of COCl₂ in toluene followed by solvent removal to yield the isocyanate intermediate VI. Reaction of the isocyanate intermediate VI with an alkylamine, aminoalkyl piperidine or tetrahydropyridine compound VIII produces the urea linked Formula I product in good overall yield.

The alkyl amines, such as the propanamines are produced by known processes. The amines can be produced from the appropriate secondary amines by conjugate addition to acrylonitrile in methanol. The reaction product is then hydrogenated catalytically in the presence of a Raney nickel catalyst in methanol to yield the amine as follows.

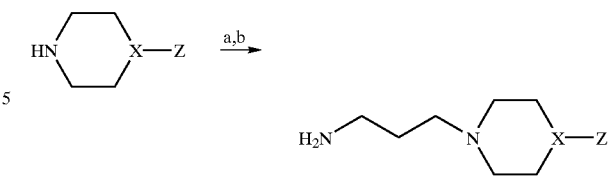

a: acrylonitrile, MeOH, Δ. b: H₂, NH₃, Raney Nickel, MeOH.

The alkyl piperazine can be synthesized by N-alkylation of the piperazine followed by removal of the Boc protecting groups as follows.

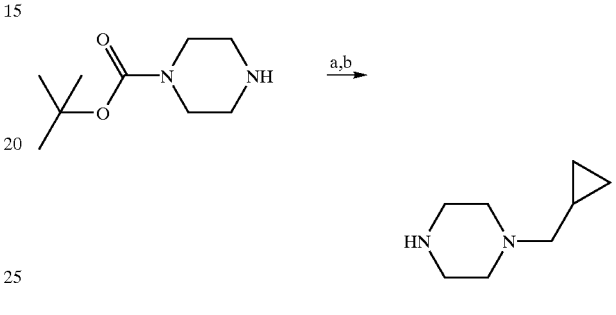

a: (Bromomethyl)cyclopropane, K₂CO₃, MeCN, Δ. b: 3N HCl, MeOH.

The Boc protecting group can also be cleaved from the intermediate to produce the unsubstituted piperazine derivative as follows.

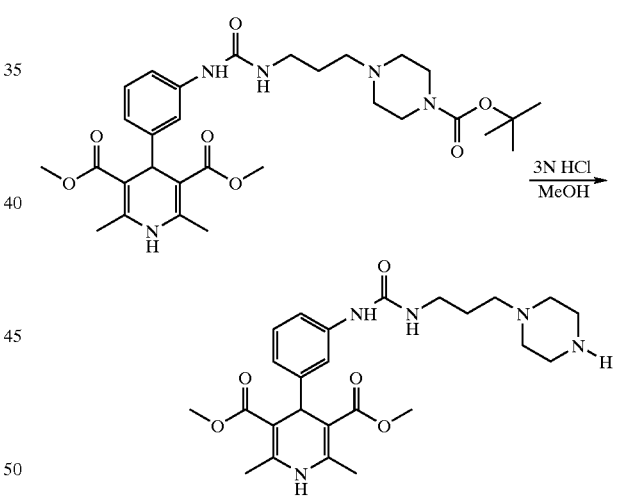

The parallel synthesis of the 4-amino piperidines is shown in Scheme 2. The ketal is converted to a ketone by transketalization in 6N HCl and acetone. The resulting ketone is then treated with a primary or secondary amine at acidic pH in the presence of sodium triacetoxyborohydride to produce the derivatives of Formula I. The final products of Formula I produced by this synthesis were isolated in purities of greater than 70% as determined by HPLC. A number of the reactions produced the alcohol as an additional or sole product, presumably due to insufficient acid in the reaction mixture, or a poorly active amine.

The aminopiperidine derivatives, where R⁵ is fluorine, are synthesized from the aniline as shown in Scheme 3. The aniline is treated with phosgene in tetrahydrofuran followed by addition to propanamine to yield the urea. Subsequent deprotection of the ketal group on the urea by transketalization with HCl and acetone yields the ketone. Reductive amination of the urea with isoamylamine in the presence of sodium triacetoxyborohydride produced the aminopiperidine. The piperidine and piperazine derivatives can be produced by an alternative Scheme 4. The starting aniline is reacted with the thiocarbonyldiimidazole in THF to produce the isothiocyanate (VII). The isothiocyanate (VII) is then reacted with the appropriate propylamine to produce the thiourea derivatives (VII). The thiourea is reacted with mercuric oxide in the presence of catalytic sulfur in dimethylformamide to produce the urea of Formula I. The S-oxo and S,S-dioxo thiomorpholine derivatives 28 and 29 were synthesized by the oxidation of the thiomorpholine, example 25 with Oxone, as shown in Scheme 5.

The compounds of the invention demonstrate binding affinity at NPY $Y_1$ receptors. This pharmacologic activity is assayed in SK-N-MC (human neuroblastoma) cell membranes using iodine-125-labeled I-PYY as a radioligand. The compounds of Formula I had good binding affinities as evidenced by $IC_{50}$ values being about 10 μM or less at NPY $Y_1$ receptors. Preferred compounds have $IC_{50}$ values less than 100 nM and most preferred compounds have $IC_{50}$ values of less than 10 nM.

Pharmacologically, the compounds of Formula I act as selective NPY antagonists at NPY $Y_1$ receptor sites. As such, the compounds of Formula I are of value in the treatment of a wide variety of clinical conditions which are characterized by the presence of an excess of neuropeptide Y. Thus, the invention provides methods for the treatment or prevention of a physiological disorder associated with an excess of neuropeptide Y, which method comprises administering to a mammal in need of treatment an effective amount of a compound of Formula I or a pharmaceutically acceptable salt, solvate or prodrug thereof. The term "physiological disorder associated with an excess of neuropeptide Y" encompasses those disorders associated with an inappropriate stimulation of neuropeptide Y receptors, regardless of the actual amount of neuropeptide Y present in the locale.

These physiological disorders include:
disorders or diseases pertaining to the heart, blood vessels or the renal system, such as vasospasm, heart failure, shock, cardiac hypertrophy, increased blood pressure, angina, myocardial infarction, sudden cardiac death, congestive heart failure, arrhythmia, peripheral vascular disease, and abnormal renal conditions such as impaired flow of fluid, abnormal mass transport, or renal failure;
conditions related to increased sympathetic nerve activity for example, during or after coronary artery surgery, and operations and surgery in the gastrointestinal track;
cerebral diseases and diseases related to the central nervous system, such as cerebral infarction, neurodegeneration, epilepsy, stroke, and conditions related to stroke, cerebral vasospasm and hemorrhage, depression, anxiety, schizophrenia, dementia, seizure, and epilepsy;
conditions related to pain or nociception;
diseases related to abnormal gastrointestinal motility and secretion, such as different forms of ileus, urinary incontinence, and Crohn's disease;
abnormal drink and food intake disorders, such as obesity, anorexia, bulemia, and metabolic disorders;
diseases related to sexual dysfunction and reproductive disorders such as benign prostatic hyperplasia and male erectile dysfunction;
conditions or disorders associated with inflammation;
respiratory diseases, such as asthma and conditions related to asthma and bronchoconstriction;
diseases related to abnormal hormone release, such as leutinizing hormone, growth hormone, insulin and prolactin; and
sleep disturbance and diabetes.

There is evidence that NPY contributes to certain symptoms in these disorders, such as, hypertension, eating disorders, and depression/anxiety, as well as circadian rhythms. Compounds of this invention are expected to be useful in treating these disorders as well as sleep disturbance and diabetes.

Selected compounds are tested further for their ability to block or stimulate NPY-induced feeding in test animals by intraperitoneal administration to the animal prior to inducing feeding behavior with NPY. Taken together, these tests indicate that the compounds of this invention would be useful anorexiants and would function as anti-obesity agents with further use in various clinical eating disorders. Thus, another aspect of the invention concerns a process for reducing food intake in an obese mammal or a mammal with an eating disorder. The process comprises systemic administration to such a mammal of an anorexiant-effective dose of a Formula I compound or a pharmaceutically acceptable acid addition salt and/or hydrate thereof.

On the basis of pharmacologic testing, an effective dose given parenterally could be expected to be in a range of about 0.05 to 1 mg/kg body weight and if given orally would be expected to be in the range of about 1 to 50 mg/kg body weight.

For clinical applications, however, the dosage and dosage regimen must in each case be carefully adjusted, utilizing sound professional judgment and considering the age, weight and condition of the recipient, the route of administration and the nature and gravity of the illness. Generally, the compounds of the instant invention will be administered in the same manner as for available anorexiant drugs such as Diethylpropion, Mazindol, or Phentermine and the daily oral dose would comprise from about 70 to about 1400 mg, preferably 500 to 1000 mg administered from 1 to 3 times a day. In some instances, a sufficient therapeutic effect can be obtained at lower doses while in others, larger doses will be required.

The term systemic administration as used herein refers to oral, buccal, transdermal, rectal, and parenteral (i.e. intramuscular, intravenous, and subcutaneous) routes. Generally, it will be found that when a compound of the present invention is administered orally, which is the preferred route, a larger quantity of reactive agent is required to produce the same effect as a smaller quantity given parenterally. In accordance with good clinical practice, it is preferred to administer the instant compounds at a concentration level that will produce effective anoretic effects without causing any harmful or untoward side effects. Similarly, the instant compounds can be administered to treat the various diseases, conditions, and disorders listed above.

Therapeutically, the compounds of Formula I are generally given as pharmaceutical compositions comprised of an effective anorectic amount of a compound of Formula I or a pharmaceutically acceptable acid addition salt thereof and a pharmaceutically acceptable carrier. Pharmaceutical compositions for effecting such treatment will contain a major or minor amount, e.g. from 95 to 0.5% of at least one compound of the present invention in combination with the pharmaceutical carrier. The carrier comprises one or more solid, semi-solid, or liquid diluent, filler, and formulation adjuvant that is non-toxic, inert and pharmaceutically acceptable.

Such pharmaceutical compositions are preferably in dosage unit forms; i.e., physically discrete units containing a predetermined amount of the drug corresponding to a fraction or multiple of the dose which is calculated to produce the desired therapeutic response. The dosage units can contain 1, 2, 3, 4, or more single doses, or, alternatively, one-half, one-third, or one-fourth of a single dose. A single dose preferably contains an amount sufficient to produce the desired therapeutic effect upon administration at one application of one or more dosage units according to the predetermined dosage regimen usually a whole, half, third, or quarter of the daily dosage administered once, twice, three, or four times a day. Other therapeutic agents can also be present.

Pharmaceutical compositions which provide from about 50 to 1000 mg of the active ingredient per unit dose are preferred and are conventionally prepared as tablets, lozenges, capsules, powders, transdermal patches, aqueous or oily suspensions, syrups, elixirs, and aqueous solutions. Preferred oral compositions are in the form of tablets or capsules and may contain conventional excipients such as binding agents (e.g. syrup, acacia, gelatin, sorbitol, tragecanth, or polyvinylpyrrolidone), fillers (e.g. lactose, sugar, maize-starch, calcium phosphate, sorbitol, or glycine), lubricants (e.g. magnesium stearate, talc, polyethylene glycol or silica), disintegrants (e.g. starch) and wetting agents (e.g. sodium lauryl sulfate).

Solutions or suspensions of a Formula I compound with conventional pharmaceutical vehicles are generally employed for parenteral compositions such as an aqueous solution for intravenous injection or an oily suspension for intramuscular injection. Such compositions having the desired clarity, stability and adaptability for parenteral use are obtained by dissolving from 0.1% to 10% by weight of the active compound in water or a vehicle consisting of a polyhydric aliphatic alcohol such as glycerin, propylene glycol, and polyethylene glycols or mixtures thereof. The polyethylene glycols consist of a mixture of non-volatile, usually liquid, polyethylene glycols which are soluble in both water and organic liquids and which have molecular weights from about 200 to 1500.

Description of the Specific Embodiments

The compounds of Formula I were prepared in the following Examples. All catalytic hydrogenations were performed with Parr Hydrogenators (Parr Instrument Co.) Bulb-to-bulb distillations were carried out on a Kugelrohr apparatus (Aldrich). Solvate removal from solids, when noted, was carried out under vacuum drying overnight in an Abderhalden drying pistol over refluxing ethanol. All melting points were obtained using a Thomas-Hoover melting point apparatus and are uncorrected. $^1$H and $^{13}$C NMR were obtained using a Bruker AM-300 NMR spectrometer at 300 and 75.5 MHz, respectively. NMR solvents used were deuterochloroform (CDCl$_3$), methyl-d$_6$-sulfoxide (DMSO-d$_6$) and deuterium oxide (D$_2$O).

While many of the synthetic intermediates and starting compounds are commercially available, they are also available via synthetic methods described in previous patents directed to this series of NPY antagonists such as U.S. Pat. Nos. 5,668,151 and 6,001,836 which are incorporated in their entirety herein.

EXAMPLE 1

Preparation of 1-(Cyclopropylmethyl)piperazine dihydrochloride

A solution of (bromomethyl)cyclopropane (27 g, 110 mmol) and 1-(tert-butoxycarbonyl)piperazine (18.6 g, 100 mmol) in MeCN (300 mL) containing K$_2$CO$_3$ (14 g) was refluxed for 3 hours. The solvent was then removed in vacuo, and the residue was taken up in water and extracted with CH$_2$Cl$_2$. The organic extract was then dried (Na$_2$SO$_4$), and the solvent was removed in vacuo. The Boc-protected intermediate was then isolated by bulb-to-bulb distillation to afford a colorless oil (23.0 g, 96% yield). This material (22.5 g, 94 mmol) was taken up in 3N methanolic HCl (150 mL, from con. HCl and MeOH) and stirred overnight. The solvent was then removed in vacuo, and the residual water was removed azeotropically with n-propanol. The residue was triturated in ether, and the resulting solid was collected by filtration. After heating overnight in a drying pistol. The compound was obtained (20.1 g, quant.): $^1$H NMR (D$_2$O) δ3.57 (br m, 8H), 3.14 (d, 2H, J=7.5 Hz), 1.08 (m, 1H), 0.70 (m, 2H), 0.37 (m, 2H); $^{13}$C NMR (D$_2$O) δ64.8, 50.7, 43.4, 7.4, 6.5. Anal Calcd for C$_8$H$_{16}$N$_2$.2HCl: C, 45.08;H, 8.51; N, 13.14. Found: C, 44.89; H, 8.56; N, 13.19.

EXAMPLE 2

General Method for the Synthesis of Propanamines

Solutions of secondary amines (1.0 eq) and acrylonitrile (1.2 eq) in MeOH (containing sufficient Et$_3$N to neutralize any acid salts present) were refluxed for 2 hours. If a secondary amine was charged as a free base, the solvent was removed in vacuo at this time to afford the desired propanenitrile intermediate without further purification. Where secondary amines were acid (HCl or HBr) salts, the solvent was removed in vacuo, and the residue was taken up in water and then extracted with CH$_2$Cl$_2$. The organic extracts were dried (Na$_2$SO$_4$) and the solvent was removed in vacuo to afford the desired propanenitrile intermediates. These compounds were then taken up in MeOH:30% aq NH$_3$ (85:15) containing Raney nickel, and hydrogenated at 50 psi for 30 min. The catalyst was then removed by filtration over Celite, and the solvent was removed in vacuo from the filtrate. The desired propanamines were then isolated by bulb-to-bulb distillation. Overall yields from secondary amines are reported. The particular propanamines obtained are as follows:

(a) 4-Propyl-1-piperazinepropanamine

This compound was obtained as a colorless oil (69% yield) according to the above process. $^1$H NMR (CDCl$_3$) δ2.68 (t, 2H, J=6.9 Hz), 2.41 (m, 8H), 2.34 (t, 2H, J=7.2 Hz), 2.25 (m, 2H), 1.63 (s, 2H), 1.60 (m, 2H), 1.42 (m, 2H), 0.83 (t, 3H, J=7.5 Hz); $^{13}$C NMR (CDCl$_3$) δ50.8, 56.6, 53.4, 53.3, 40.9, 30.5, 20.1, 12.0. Anal Calcd for C$_{10}$H$_{23}$N$_3$.0.2H$_2$O: C, 63.58; H, 12.49; N, 22.24. Found: C, 63.21;H, 12.58; N, 22.22.

(b) 4-Cyclopropyl-1-piperazinepropanamine

This compound was obtained as a colorless oil (78% yield): $^1$H NMR (CDCl$_3$) δ2.72 (t, 2H, J=6.6 Hz), 2.62 (m, 4H), 2.41 (m, 4H), 2.37 (t, 2H, J=7.5 Hz), 1.67 (s, 2H), 1.57 (m, 3H), 0.39 (m, 4H); $^{13}$C NMR (CDCl$_3$) δ56.7, 53.5, 53.4, 41.0, 38.6, 30.6, 5.8.HRMSCalcd for C$_{10}$H$_{22}$N$_3$: 184.1820. Found: 184.1820.

(c) 4-(2-Methylpropyl)-1-piperazinepropanamine

This compound was obtained as a colorless oil (81% yield): $^1$H NMR (CDC$_3$) δ2.68 (t, 2H, J=6.9 Hz), 2.32 (m, 10H), 2.12 (d, 2H, J=7.2 Hz), 1.70 (m, 1H), 1.58 (m, 4H), 0.83 (d, 6H, J=6.6 Hz); $^{13}$C NMR (CDCl$_3$) δ67.0, 56.6, 53.6, 53.5, 40.9, 30.5, 25.4, 21.0. Anal Calcd for C$_{11}$H$_{25}$N$_3$.0.2H$_2$O: C, 65.10; H, 12.62; N, 20.71. Found: C, 64.78; H, 12.42; N, 20.58.

(d) 4-(Cyclopropylmethyl)-1-piperazinepropanamine

This compound was obtained as a colorless oil (76% yield): $^1$H NMR (CDCl$_3$) δ2.64 (t, 2H, J=6.9 Hz), 2.41 (m, 8H), 2.31 (t, 2H, J=7.2 Hz), 2.14 (d, 2H, J=6.6 Hz), 1.54 (m, 4H), 0.77 (m, 1H), 0.41 (m, 2H), 0.02 (m, 2H); $^{13}$C NMR (CDCl$_3$) δ63.8, 56.6, 53.3, 40.9, 30.5, 8.3, 3.9. Anal Calcd for C$_{11}$H$_{23}$N$_3$.0.3H$_2$O: C, 65.17; H, 11.73; N, 20.73. Found: C, 64.97; H, 11.77; N, 20.67.

(e) 4-(1,1-Dimethylethyl)-1-piperazinepropanamine

This compound was obtained as a colorless oil (74% yield): $^1$H NMR (CDCl$_3$) δ2.70 (t, 2H, J=6.6 Hz), 2.56 (m, 4H), 2.44 (m, 4H), 2.34 (t, 2H, J=7.5 Hz), 1.67 (s,2H), 1.60 (m, 2H), 1.02 (s, 9H); $^{13}$C NMR (CDCl$_3$) δ56.5, 54.1, 53.6, 45.6, 40.9, 30.5, 25.9. Anal Calcd for C$_{11}$H$_{25}$N$_3$.0.3H$_2$O: C, 64.53; H, 12.60; N, 20.52. Found: C, 64.65; H, 12.72; N, 20.42.

(f) 4-Cyclopentyl-1-piperazinepropanamine

This compound was obtained as a colorless oil (67% yield): $^1$H NMR (CDCl$_3$) δ2.71 (t, 2H, J=6.9 Hz), 2.44 (m, 9H), 2.36 (t, 2H, J=6.9 Hz), 1.82 (m, 2H), 1.63 (m, 6H), 1.46 (m, 2H), 1.36 (m, 2H); $^{13}$C NMR (CDCl$_3$) δ67.6, 56.6, 53.4, 52.4, 40.9, 30.5, 24.2. Anal Calcd for C$_{12}$H$_{25}$N$_3$.0.5H$_2$O: C, 65.41; H, 11.89; N, 19.07. Found: C, 65.09; H, 12.02; N, 18.92.

(g) 4-(3-Aminopropyl)-1-piperazinecarboxylic acid, 1,1-dimethylethyl ester

This compound was obtained as a colorless oil (94% yield): $^1$H NMR (CDCl$_3$) δ3.35 (m, 4H), 2.68 (t, 2H, J=6.9 Hz), 2.32 (m, 6H), 1.56 (m, 2H), 1.38 (s, 9H), 1.33 (s, 2H); $^{13}$C NMR (CDCl$_3$) δ154.8, 79.6, 56.5, 53.1, 43.7, 40.7, 30.4, 28.4. Anal Calcd for C$_{122}$H$_{25}$N$_3$O$_2$.0.5H$_2$O: C, 57.11; H, 10.38; N, 16.65. Found: C, 57.45; H, 10.09; N, 16.66.

(h) 1,4-Dioxa-8-azaspiro[4.5]decane-8-propanamine

This compound was obtained as a colorless oil (quant.): $^1$H NMR (CDCl$_3$) δ3.90 (s, 4H), 2.70 (t, 2H, J=6.9 Hz), 2.47 (m, 4H), 2.37 (t, 2H, J=7.2 Hz), 1.69 (m, 4H), 1.60 (m, 4H); $^{13}$C NMR (CDCl$_3$) δ107.3, 64.2, 56.2, 51.5, 40.9, 34.9, 30.9. Anal Calcd for C$_{10}$H$_{20}$N$_2$O$_2$.0.4H$_2$O: C, 57.89; H, 10.11; N, 13.50. Found: C, 58.15; H, 9.95; N, 13.30.

EXAMPLE 3

General Procedure for the Synthesis of Ureas

Solutions of the respective propanamines (1.5 eq) and an isocyanate (1.0 eq) in MeCN were stirred for 2–18 hours, and the solvent was then removed in vacuo. The residues were taken up in CH$_2$Cl$_2$, rinsed with water, and then extracted with 1N HCl. The acidic extracts were then made basic with saturated Na$_2$CO$_3$ and extracted with CH$_2$Cl$_2$. The organic extracts were dried (Na$_2$SO$_4$), and the solvent was then removed in vacuo. The residues were taken up in MeOH and acidified with a slight excess of 1 N HCl/$_2$O. The solvent was removed in vacuo, and the resulting solids were heated overnight in a drying pistol to afford the products.

The specific ureas obtained are identified in Examples 4–15.

EXAMPLE 4

4-[3-[[[[3-(4-Ethyl-1-piperazinyl)propyl]amino]carbonyl]amino]phenyl]-1,4-dihydro-2,6-dimethyl-3,5-pyridinedicarboxylic acid, dimethyl ester dihydrochloride This compound was obtained as a pale amber solid (60% yield): mp 120–125° C. (sintered); $^1$H NMR (DMSO-d$_6$) δ11.76 (br s, 2H), 8.96 (s, 1H), 8.71 (s, 1H), 7.27 (d, 1H, J=8.1 Hz), 7.10 (s, 1H), 7.03 (t, 1H, J=7.2 Hz), 6.65 (d, 1H, J=7.8 Hz), 6.45 (m, 1H), 4.84 (s, 1H), 3.74 (m, 4H), 3.55 (s, 6H), 3.43 (m, 6H), 3.16 (m, 4H), 2.26 (s, 6H), 1.87 (m, 2H), 1.26 (t, 3H, J=7.2 Hz); $^{13}$C NMR (DMSO-d$_6$) δ167.4, 155.4,148.1, 145.6,140.2, 128.2, 119.8,116.5,115.5, 101.3, 53.8, 50.8, 50.6, 48.1, 47.4, 38.3, 36.3, 24.4,18.2, 8.7. Anal Calcd for C$_{27}$H$_{39}$N$_5$O$_5$.2HCl. H$_2$O: C, 53.64; H, 7.17; N, 11.58. Found: C, 53.85; H, 7.24; N, 11.52.

EXAMPLE 5

4-[3-[[[[3-(4-Propyl-1-piperazinyl)propyl]amino]carbonyl]amino]phenyl]-1,4-dihydro-2,6-dimethyl-3,5-pyridinedicarboxylic acid, dimethyl ester dihydrochloride This compound was obtained as a pale amber solid (82% yield): mp 190–200° C. (sintered); $^1$H NMR (DMSO-d$_6$) δ11.77 (br s, 2H), 8.96 (s, 1H), 8.70 (s, 1H), 7.26 (d, 1H, J=8.1 Hz), 7.09 (s, 1H), 7.02 (t, 1H, J=7.8 Hz), 6.65 (d, 1H, J=7.8 Hz), 6.45 (m, 1H), 4.84 (s, 1H), 3.73 (m, 4H), 3.55 (s, 6H), 3.46 (m, 6H), 3.15 (m, 2H), 3.07 (m, 2H), 2.26 (s, 6H), 1.87 (m, 2H), 1.71 (m, 2H), 0.91 (t, 3H, J=7.5 Hz); $^{13}$C NMR (DMSO-d$_6$) δ167.4,155.4, 148.1, 145.6, 140.2, 128.2, 119.8, 116.5, 115.5, 101.3, 57.1, 53.8, 50.6, 48.0, 35.3, 36.2, 24.3, 18.2, 15.6, 10.8. Anal Calcd for C$_{28}$H$_{41}$N$_5$O$_5$.2HCl.H$_2$O: C, 54.37; H, 7.33; N, 11.32. Found: C, 54.63; H, 7.25; N, 11.29.

EXAMPLE 6

4-[3-[[[[3-[4-(1-Methylethyl)-1-piperazinyl]propyl]amino]carbonyl]amino]-phenyl]-1,4-dihydro-2,6-dimethyl-3,5-pyridinedicarboxylic acid, dimethyl ester dihydrochloride This compound was obtained as a pale amber solid (66% yield): mp 170–180° C. (sintered); $^1$H NMR (DMSO-d$_6$) δ11.76 (br s, 1H), 8.94 (s, 1H), 8.66 (s, 1H), 7.27 (d, 1H, J=9.0 Hz), 7.09 (s, 1H), 7.03 (t, 1H, J=7.8 Hz), 6.66 (d, 1H, J=7.5 Hz), 6.40 (m, 1H), 4.84 (s, 1H), 3.74 (m, 2H), 3.61 (m, 2H), 3.55 (s, 6H), 3.50 (m, 5H), 3.16 (m, 4H), 2.26 (s, 6H), 1.87 (m, 2H), 1.29 (d, 6H, J=6.6 Hz); $^{13}$C NMR (DMSO-d$_6$) δ167.4, 155.4, 148.1, 145.6, 140.2, 128.2, 119.8, 116.5, 115.5, 101.3, 57.1, 53.7, 50.7, 48.1, 44.1, 38.4, 36.3, 24.4, 18.2, 16.0. AnalCalcd for C$_{28}$H$_{41}$N$_5$O$_5$.2HCl.1.5H$_2$O: C, 53.59; H, 7.39; N, 11.16. Found: C, 53.77; H, 7.39; N, 11.11.

EXAMPLE 7

4-[3-[[[[3-(4-Cyclopropyl-1-piperazinyl)propyl]amino]carbonyl ]amino]-phenyl]-1,4-dihydro-2,6-dimethyl-3,5-pyridinedicarboxylic acid, dimethyl ester dihydrochloride This compound was obtained as a pale amber solid (69% yield): mp 170–180° C. (sintered); $^1$H NMR (DMSO-d$_6$) δ8.94 (s, 1H), 8.69 (s, 1H), 7.26 (d, 1H, J=9.0 Hz), 7.09 (s, 1H), 7.03 (t, 1H, J=7.8 Hz), 6.65 (d, 1H, J=7.5 Hz), 6.45 (m, 1H), 4.84 (s, 1H), 3.66 (m, 6H), 3.55 (s, 6H), 3.40 (br m, 3H), 3.16 (m, 4H), 2.26 (s, 6H), 1.87 (m, 2H), 1.05 (m, 2H), 0.77 (m, 2H); $^{13}$C NMR (DMSO-d$_6$) δ167.4, 155.4,148.1, 145.6, 140.2, 128.2, 119.8, 116.5, 115.5, 101.3, 50.6, 38.4, 36.2, 30.7, 24.4, 18.2, 4.0. Anal Calcd for C$_{28}$H$_{39}$N$_5$O$_5$.2HCl.1.5H$_2$O: C, 53.76; H, 7.09; N, 11.19. Found: C, 53.65; H, 7.15; N, 11.15.

EXAMPLE 8

4-[3-[[[[3-(4-Butyl-1-piperazinyl)propyl]amino]carbonyl]amino]phenyl]-1,4-dihydro-2,6-dimethyl-3,5-pyridinedicarboxylic acid, dimethyl ester dihydrochloride This compound was obtained as a pale amber solid (69% yield): mp 145–150° C. (sintered); $^1$H NMR (DMSO-d$_6$)

δ11.74 (br s, 2H), 8.95 (s, 1H), 8.69 (s, 1H), 7.27 (d, 1H, J=8.1 Hz), 7.09 (s, 1H), 7.02 (t, 1H, J=8.1 Hz), 6.65 (d, 1H, J=7.8 Hz), 6.44 (m, 1H), 4.84 (s, 1H), 3.73 (m, 4H), 3.55 (s, 6H), 3.46 (m, 6H), 3.15 (m, 4H), 2.26 (s, 6H), 1.87 (m, 2H), 1.66 (m, 2H), 1.32 (m, 2H), 0.90 (t, 3H, J=7.2 Hz); $^{13}$C NMR (DMSO-$d_6$) δ167.5, 155.5, 148.1, 145.6, 140.3, 128.2, 119.8, 116.5, 115.5, 101.3, 55.4, 53.8, 50.7, 48.1, 38.4, 36.3, 24.9, 24.3, 19.3, 18.5, 18.2, 13.5. Anal Calcd for $C_{29}H_{43}N_5O_5 \cdot 2HCl \cdot 1.5H_2O$: C, 54.29; H, 7.54; N, 10.91. Found: C, 54.49; H, 7.52; N, 10.89.

EXAMPLE 9

4-[3-[[[[3-[4-(2-Methylpropyl)-1-piperazinyl]propyl]amino]carbonyl]-amino]phenyl]-1,4-dihydro-2,6-dimethyl-3,5-pyridinedicarboxylic acid, dimethyl ester dihydrochloride This compound was obtained as a pale amber solid (67% yield): mp 165–170° C. (sintered); $^1$H NMR (DMSO-$d_6$) δ8.96 (s, 1H), 8.72 (s, 1H), 7.27 (d, 1H, J=8.4 Hz), 7.10 (s, 1H), 7.03 (t, 1H, J=7.8 Hz), 6.65 (d, 1H, J=7.5 Hz), 6.47 (m, 1H), 4.84 (s, 1H), 3.70 (m, 2H), 3.63 (m, 4H), 3.55 (s, 6H), 3.41 (m, 4H), 2.97 (m, 2H), 2.26 (s, 6H), 2.07 (m, 1H), 1.87 (m, 2H), 0.99 (d, 6H, J=6.6 Hz); $^{13}$C NMR (DMSO-$d_6$) δ167.4, 155.4, 148.1, 145.6, 140.2, 128.2, 119.8, 116.5, 115.4, 101.3, 63.2, 53.8, 50.6, 48.7, 47.7, 38.3, 36.2, 24.2, 23.2, 20.5, 18.2. Anal Calcd for $C_{29}H_{43}N_5O_5 \cdot 2HCl \cdot 1.5H_2O$: C, 54.29; H, 7.54; N, 10.91. Found: C, 54.11; H, 7.60; N, 10.79.

EXAMPLE 10

4-[3-[[[[3-[4-(Cyclopropylmethyl)-1-piperazinyl]propyl]amino]carbonyl]-amino]phenyl]-1,4-dihydro-2,6-dimethyl-3,5-pyridinedicarboxylic acid, dimethyl ester dihydrochloride This compound was obtained as a pale amber solid (73% yield): mp 145–150° C. (sintered); $^1$H NMR (DMSO-$d_6$) δ11.77 (br s, 2H), 8.96 (s, 1H), 8.70 (s, 1H), 7.27 (d, 1H, J=8.1 Hz), 7.10 (s, 1H), 7.03 (t, 1H, J=7.8 Hz), 6.65 (d, 1H, J=7.8 Hz), 6.45 (m, 1H), 4.84 (s, 1H), 3.77 (m, 4H), 3,55 (s, 6H), 3.48 (m, 4H), 3.16 (m, 4H), 3.08 (m, 2H), 2.26 (s, 6H), 1.87 (m, 2H), 1.12 (m, 1H), 0.63 (m, 2H), 0.42 (m, 2H); $^{13}$C NMR (DMSO-$d_6$) δ167.4, 155.4, 148.1, 145.6, 140.2, 128.2, 119.8, 116.5, 155.5, 101.3, 59.7, 53.8, 50.6, 48.0, 47.6, 38.4, 36.2, 24.3, 18.2, 4.9, 4.1. Anal Calcd for $C_{29}H_{41}N_5O_5 \cdot 2HCl \cdot 1.75H_2O$: C, 54.08; H, 7.28; N, 10.87. Found: C, 54.05; H, 7.30; N, 10.78.

EXAMPLE 11

4-[3-[[[[3-[4-(1,1-Dimethylethyl)-1-piperazinyl]propyl]amino]carbonyl]-amino]phenyl]-1,4-dihydro-2,6-dimethyl-3,5-pyridinedicarboxylic acid, dimethyl ester dihydrochloride This compound was obtained as a pale amber solid (70% yield): mp 175–180° C. (sintered); $^1$H NMR (DMSO-$d_6$) δ11.78 (br s, 2H), 8.95 (s, 1H), 8.65 (s, 1H), 7.27 (d, 1H, J=8.1 Hz), 7.09 (s, 1H), 7.03 (t, 1H, J=7.8 Hz), 6.65 (d, 1H, J=7.8 Hz), 6.40 (m, 1H), 4.84 (s, 1H), 3.74 (m, 4H), 3.63 (m, 4H), 3.55 (s, 6H), 3.16 (m, 4H), 2.25 (s, 6H), 1.87 (m, 2H), 1.37 (s, 9H); $^{13}$C NMR (DMSO-$d_6$) δ167.4, 155.4, 148.1, 145.6, 140.2, 128.2, 119.8, 116.5, 115.5, 101.3, 63.3, 53.6, 50.7, 48.2, 42.6, 38.4, 36.3, 24.3, 23.5, 18.2. Anal Calcd for $C_{29}H_{43}N_5O_5 \cdot 2HCl \cdot 2H_2O$: C, 53.53; H, 7.59; N, 10.76. Found: C, 53.34; H, 7.63; N, 10.62.

EXAMPLE 12

4-[3-[[[[3-(4-Cyclopentyl-1-piperazinyl)propyl]amino]carbonyl]amino]-phenyl]-1,4-dihydro-2,6-dimethyl-3,5-pyridinedicarboxylic acid, dimethyl ester dihydrochloride This compound was obtained as a white solid (80% yield): mp 195–200° C. (sintered); $^1$H NMR (DMSO-$d_6$) δ12.03 (br s, 1H), 11.77 (br s, 1H), 8.95 (s, 1H), 8.68 (s, 1H), 7.26 (d, 1H, J=9.0 Hz), 7.09 (s, 1H), 7.03 (t, 1H, J=7.8 Hz), 6.65 (d, 1H, J=7.5 Hz), 6.42 (m, 1H), 4.84 (s, 1H), 3.72 (m, 4H), 3.55 (s, 6H), 3.48 (m, 4H), 3.16 (m, 4H), 2.26 (s, 6H), 2.02 (m, 2H), 1.84 (m, 6H), 1.54 (m, 2H); $^{13}$C NMR (DMSO-$d_6$) δ167.4, 155.4, 148.1, 145.6, 140.2, 128.2, 119.8, 116.5, 115.5, 101.3, 66.7, 53.7, 50.7, 48.2, 47.3, 38.4, 36.3, 27.3, 24.3, 23.4, 18.2. Anal Calcd for $C_{30}H_{43}N_5O_5 \cdot 2HCl \cdot 1.3H_2O$: C, 55.43; H, 7.38; N, 10.77. Found: C, 55.61; H, 7.44; N, 10.65.

EXAMPLE 13

4-[3-[[[[3-[4-[(1,1-Dimethylethoxy)carbonyl]-1-piperazinyl]propyl]amino]-carbonyl]amino]phenyl]-1,4-dihydro-2,6-dimethyl-3,5-pyridinedicarboxylic acid, dimethyl ester This compound was obtained as a white solid (63% yield): mp 125–130° C. (sintered); $^1$H NMR (DMSO-$d_6$) δ8.88 (s, 1H), 8.39 (s, 1H), 7.24 (d, 1H, J=8.1 Hz), 7.09 (s, 1H), 7.02 (t, 1H, J=7.8 Hz), 6.65 (d, 1H, J=7.5 Hz), 6.10 (m, 1H), 4.84 (s, 1H), 3.55 (s, 6H), 3.34 (m, 6H), 3.08 (m, 2H), 2.33 (m, 4H), 2.25 (s, 6H), 1.60 (m, 2H), 1.39 (s, 9H); $^{13}$C NMR (DMSO-$d_6$) δ167.4, 155.2, 153.7, 148.1, 145.5, 140.3, 128.2, 119.7, 116.4, 155.5, 101.4, 78.8, 55.1, 52.3, 50.6, 38.4, 37.2, 26.7, 18.2. Anal Calcd for $C_{30}H_{43}N_5O_7 \cdot 0.7H_2O$: C, 60.22; H, 7.48; N, 11.71. Found: C, 60.00; H, 7.25; N, 11.68.

EXAMPLE 14

4-[3-[[[[3-(1,4-Dioxa-8-azaspiro[4.5]decan-8-yl)propyl]amino]carbonyl]-amino]phenyl]-1,4-dihydro-2,6-dimethyl-3,5-pyridinedicarboxylic acid, dimethyl ester This compound was obtained as a white solid (76% yield): mp 100–105° C. (sintered); $^1$H NMR (DMSO-$d_6$) δ8.88 (s, 1H), 8.38 (s, 1H), 7.23 (d, 1H, J=8.1 Hz), 7.09 (s, 1H), 7.02 (t, 1H, J=7.8 Hz), 6.65 (d, 1H, J=7.5 Hz), 6.08 (t, 1H, J=5.4 Hz), 4.84 (s, 1H), 3.86 (s, 4H), 3.55 (s, 6H), 3.41 (m, 2H), 3.07 (m, 2H), 2.50 (m, 2H), 2.40 (m, 2H), 2.25 (s, 6H), 1.62 (m, 6H); $^{13}$C NMR (DMSO-$d_6$) δ167.4, 155.2, 148.1, 145.5, 140.3, 128.2, 119.7, 116.4, 155.5, 106.2, 101.4, 63.6, 54.8, 50.8, 50.6, 38.4, 37.3, 34.1, 27.1, 18.2. Anal Calcd for $C_{28}H_{38}N_4O_7 \cdot 0.5H_2O$: C, 60.97; H, 7.13; N, 10.16. Found: C, 60.84; H, 7.02; N, 10.13.

EXAMPLE 15

4-[3-[[[[3-(1-Piperazinyl)propyl]amino]carbonyl]amino]phenyl]-1,4-dihydro-2,6-dimethyl-3,5-pyridinedicarboxylic acid, dimethyl ester dihydrochloride A solution of the compound of Example 13 (1.7 g, 2.9 mmol) in 3N methanolic HCl (from con. HCl) was stirred for 30 minutes, and the solvent was removed in vacuo, removing residual water azeotropically with n-propanol. The residue was taken up in hot n-propanol, filtered, and diluted with a threefold excess of Et$_2$O. The resulting precipitate was collected by filtration and heated overnight in a drying pistol to afford a compound as a light amber solid (1.2 g, 75% yield): mp 120–130° C. (sintered); $^1$H NMR (DMSO-d$_6$) δ9.78 (br s, 2H), 8.97 (s, 1H), 8.74 (s, 1H), 7.25 (d, 1H, J=8.1 Hz), 7.10 (s, 1H), 7.02 (t, 1H, J=7.5 Hz), 6.65 (d, 1H, J=7.8 Hz), 6.49 (m, 1H), 4.84 (s, 1H), 3.64 (m, 4H), 3.55 (s, 6H), 3.45 (m, 4H), 3.16 (m, 4H), 2.26 (s, 6H), 1.87 (m, 2H); $^{13}$C NMR (DMSO-d$_6$) δ167.4, 155.4, 145.6, 140.2, 128.2, 119.8, 116.4, 115.4, 101.3, 53.6, 50.6, 47.7, 39.8, 38.3, 36.3, 24.2,18.2. Anal Calcd for C$_{25}$H$_{35}$N$_5$O$_5$.2HCl.2H$_2$O: C, 50.51; H, 6.95; N, 11.78. Found: C, 1.02; H, 7.24; N, 11.34.

EXAMPLE 16

General Procedure for the Preparation of the 4-Fluorinated Derivatives

The starting aniline dihydropyridine is reacted with the thiocarbonyldiimidazole in THF to produce the isothiocyanate. The isothiocyanate is reacted with the piperazine propylamine or piperidine propylamine to produce the thiourea derivatives. To solutions of thioureas (45–55 mg) in DMF (2 mL) was added yellow HgO (4 eq.), S$_8$ (0.1 mg) and H$_2$O (0.2 mL), and the resulting mixtures were stirred at 75° C. overnight. The reaction mixtures were then adsorbed onto Varian SCX cartridges (1 g/6 mL, preconditioned with 20% MeOH in CH$_2$Cl$_2$, 6 mL), rinsing with 20% MeOH in CH$_2$Cl$_2$ (6 mL), and eluting the products with 2M methanolic NH$_3$ (6 mL). After solvent removal, the 4-fluorinated derivatives were isolated from the residues by recrystallization (CH$_2$Cl$_2$, Et$_2$O and hexanes).

The specific 4-fluoro derivatives synthesized are identified in Examples 17–21.

EXAMPLE 17

4-[4-Fluoro-3-[[[[3-(4-methyl-1-piperidinyl)propyl] amino]carbonyl]-amino]phenyl]-1,4-dihydro-2,6-dimethyl-3,5-pyridinedicarboxylic acid, dimethyl ester The compound was isolated as a white powder (69% yield): mp 188–190° C.; $^1$H NMR (DMSO-d$_6$) δ8.91 (s, 1H), 8.10 (s, 1H), 8.01 (dd, 1H, J=6.0 , 8.0 Hz,), 6.96 (dd, 1H, J=8.4,11.4 Hz), 6.63 (m, 1H), 6.55 (t, 1H, J=5.4 Hz), 4.83 (s, 1H), 3.55 (s, 6H), 3.07 (m, 2H), 2.84 (m, 2H), 2.33 (m, 2H), 2.26, (s, 6H), 1.91 (m, 2H), 1.57 (m, 4H), 1.31 (m, 1H), 1.13 (m, 2H), 0.87 (d, 3H, J=6.3 Hz); $^{13}$C NMR (DMSO-d$_6$) δ167.3, 154.8, 145.6, 143.7, 127.8, 127.7, 119.1, 114.1, 113.8, 101.4, 55.4, 53.3, 50.6, 38.1, 37.3, 33.7, 30.2, 26.9, 21.7, 18.2. AnaL Calcd for C$_{27}$H$_{37}$FN$_4$O$_5$.0.60H$_2$O: C, 61.49; H, 7.31; N, 10.62. Found: C, 61.46; H, 7.06; N, 10.29.

EXAMPLE 18

4-[4-Fluoro-3-[[[[3-(4-ethyl-1-piperidinyl)propyl] amino]carbonyl]amino]-phenyl]-1,4-dihydro-2,6-dimethyl-3,5-pyridinedicarboxylic acid, dimethyl ester The compound was isolated as a white powder (26% yield): mp indistinct; $^1$H NMR (CDCl$_3$) δ7.88 (dd, 1H, J=6.3, 8.8 Hz), 7.25 (s, 1H), 6.92–6.70 (m, 3H), 6.20 (br. s, 1H), 4.93 (s, 1H), 3.63 (s, 6H), 3.29 (t, 2H, J=6.0 Hz), 2.97 (d, 2H, J=10.8 Hz), 2.51 (t, 2H, J=6.6 Hz), 2.30, (s, 6H), 1.97 (m, 2H), 1.70 (m, 4H), 1.20 (m, 5H), 0.86 (t, 3H, J=7.2 Hz); $^{13}$NMR (CDCl$_3$) δ168.1, 155.6, 144.7, 144.1, 127.1, 122.5, 121.1, 114.2, 114.0,, 103.6, 56.9, 53.8, 51.0, 39.8, 39.1, 37.2, 31.7, 29.1, 25.7, 19.5, 11.3. Anal. Calcd for C$_{28}$H$_{39}$FN$_4$O$_5$.0.70H$_2$O: C, 61.91; H, 7.50; N, 10.31. Found: C, 61.89; H, 7.28; N, 10.02.

EXAMPLE 19

4-[4-Fluoro-3-[[[[3-(4-propyl-1-piperidinyl)propyl] amino]carbonyl]-amino]phenyl]-1,4-dihydro-2,6-dimethyl-3,5-pyridinedicarboxylic acid, dimethyl ester The compound was isolated as a white powder (51% yield): mp indistinct; $^1$H NMR (DMSO-d$_6$) δ8.91 (s, 1H), 8.12 (d, 1H, J=2.4 Hz), 8.01 (dd, 1H, J=6.0, 8.0 Hz,), 6.96 (dd, 1H, J=8.4, 10.8 Hz), 6.63 (m, 1H), 6.55 (t, 1H, J=5.4 Hz), 4.83 (s, 1H), 3.55 (s, 6H), 3.07 (m, 2H), 2.91 (m, 2H), 2.35 (m, 2H), 2.26, (s, 6H), 1.94 (m, 2H), 1.60 (m, 4H), 1.31–1.06 (m, 7H), 0.85 (t, 3H, J=6.9 Hz); $^{13}$C NMR (DMSO-d$_6$) δ167.3, 154.8, 145.6, 143.8, 127.8, 127.7, 119.1, 114.1, 101.4, 55.4, 53.3, 50.6, 38.1, 37.2, 34.6, 31.6, 26.7, 23.1, 19.3, 18.2, 14.2. Anal. Calcd for C$_{29}$H$_{41}$FN$_4$O$_5$.1.70H$_2$O: C, 60.55; H, 7.78; N, 9.74. Found: C, 60.24; H, 7.39; N, 9.51.

EXAMPLE 20

4-[4-Fluoro-3-[[[[3-[4-(1-methylethyl)-1-piperidinyl] propyl]amino]-carbonyl]amino]phenyl]-1,4-dihydro-2,6-dimethyl-3,5-pyridinedicarboxylic acid, dimethyl ester The compound was isolated as a white powder (75% yield): mp 176–179° C.; $^1$H NMR (DMSO-d$_6$) δ8.91 (s, 1H), 8.10 (d, 1H, J=2.4 Hz), 8.01 (dd, 1H, J=6.0, 8.1 Hz,), 6.96 (dd, 1H, J=8.4, 11.4 Hz), 6.63 (m, 1H), 6.55 (t, 1H, J=5.7 Hz), 4.83 (s,1H), 3.55 (s, 6H), 3.07 (m, 2H), 2.91 (m, 2H), 2.35–2.26 (m, 8H), 1.85 (m, 2H), 1.56 (m, 4H), 1.38 (m, 1H), 1.22 (m, 2H), 1.10 (m, 1H), 0.83 (d, 6H, J=6.6 Hz); $^{13}$C NMR (DMSO-d$_6$) δ167.3, 154.8, 145.6, 143.8, 127.8, 127.7, 119.1, 114.1, 101.4, 55.5, 53.8, 50.6, 41.8, 38.1, 37.3, 31.9, 28.8, 27.0,19.7, 18.2. Anal Calcd for C$_{29}$H$_{41}$FN$_4$O$_5$.0.50H$_2$O: C, 62.91; H, 7.65; N, 10.12. Found: C, 62.88; H, 7.57; N, 9.80.

EXAMPLE 21

4-[4-Fluoro-3-[[[[3-[4-(1,1-dimethylethyl)-1-piperidinyl]propyl]amino]-carbonyl]amino]phenyl]-1,4-dihydro-2,6-dimethyl-3,5-pyridinedicarboxylic acid, dimethyl ester The compound was isolated as a white powder (80% yield): mp 191–193° C.; $^1$H NMR (DMSO-d$_6$) δ8.91 (s, 1H), 8.09 (d, 1H, J=2.0 Hz), 8.02 (dd, 1H, J=6.6, 8.4 Hz,), 6.96 (dd, 1H, J=8.7,11.4 Hz), 6.63 (m, 1H), 6.54 (t, 1H, J=5.7 Hz), 4.83 (s, 1H), 3.55 (s, 6H), 3.07 (m, 2H), 2.91 (m, 2H), 2.26, (s, 8H), 1.76 (m, 2H), 1.56 (m, 4H), 1.18 (m, 2H), 0.95 (m, 1H), 0.82 (s, 9H); $^{13}$C NMR (DMSO-d$_6$) δ167.3, 154.8, 145.6, 143.7, 127.8, 127.7, 119.1, 114.1, 101.4, 55.5, 54.2, 50.6, 46.1, 38.1, 37.3, 31.8, 27.2, 26.4,18.2. Anal. Calcd for C$_{30}$H$_{43}$FN$_4$O$_5$.0.33H$_2$O: C, 63.82; H, 7.79; N, 9.92. Found: C, 63.82; H, 7.84; N, 9.78.

EXAMPLE 22

4-[3-[[[[3-(4-Oxo-1-piperidinyl)propyl]amino] carbonyl]amino]phenyl]-1,4-dihydro-2,6-dimethyl-3,5-pyridinedicarboxylic acid, dimethyl ester hydrochloride A solution of the compound of Example 14 (20.0 g, 36.9 mmol) in acetone (150 mL) and 6N aq HCl (150 mL) was stirred overnight under $N_2$. The resulting white precipitate was collected by filtration and rinsed with a small amount of water. A small aliquot of this material was set aside for analysis. The remainder of the material was taken up in acetone and made basic with sat. $Na_2CO_3$, resulting in the formation of a large amount of precipitate. The supernatant was decanted, and the solvent was removed in vacuo. The residue was triturated in $CH_2Cl_2$, followed by filtration, and the filtrate was dried ($Na_2SO_4$). The solvent was removed in vacuo to afford a white solid (12.7 g, 69% yield). The hydrochloride salt was obtained as a white solid: mp 70–75° C.; $^1$H NMR (DMSO-$d_6$) δ11.03 (br s, 1H), 8.93 (s, 1H), 8.67 (s, 1H), 7.27 (d, 1H, J=7.8 Hz), 7.09 (s, 1H), 7.03 (t, 1H, J=7.8 Hz), 6.66 (d, 1H, J=7.8 Hz), 6.43 (t, 1H, J=5.4 Hz), 4.84 (s, 1H), 3.68 (m, 2H), 3.56 (s, 6H), 3.18 (m, 4H), 2.89 (m, 2H), 2.48 (m, 4H), 2.26 (s, 6H), 1.87 (m, 2H); $^{13}$C NMR (DMSO-$d_6$) δ167.4, 155.5, 148.1, 145.6, 140.2, 128.2, 119.8, 116.5, 115.5, 101.3, 52.9, 50.6, 49.9, 38.4, 36.9, 36.3, 24.9, 18.2. Anal Calcd for $C_{26}H_{34}N_4O_6 \cdot HCl \cdot 2.9H_2O$: C, 53.18; H, 7.00; N, 9.54. Found: C, 53.64; H, 7.22; N, 8.99.

EXAMPLE 23

General Method for Second Lot Synthesis of Aminopiperidines

Solutions of the appropriate 4-oxopiperidine(1.0 eq) and isoamylamine or thiomorpholine (5.0 eq) in $CH_2Cl_2$, adjusted to pH 4–5 with AcOH, were stirred under $N_2$ for 1 hour, adding small amounts of MeOH as needed to dissolve any precipitated materials. To these solutions was then added NaBH(OAc)$_3$ (3.0 eq), and the resulting mixtures were then stirred overnight. The reactions were first made basic by the addition of saturated $Na_2CO_3$, and then diluted with water. The resulting organic extract was dried ($Na_2SO_4$), and the solvent was removed in vacuo. From the residues thus obtained, aminopiperidines were isolated by flash chromatography ($SiO_2$:$NH_3$/MeOH/$CH_2Cl_2$). The free base of each compound was taken up in MeOH and acidified with 2 eq of 1N HCl/Et$_2$O, and the solvent was removed in vacuo to afford the dihydrochloride salts. The aminopiperidines obtained by this method are identified in Examples 24 and 25.

EXAMPLE 24

4-[3-[[[[3-[4-[(3-Methylbutyl)amino]-1-piperidinyl] propyl]amino]-carbonyl]amino]phenyl]-1,4-dihydro-2,6-dimethyl-3,5-pyridinedicarboxylic acid, dimethyl ester dihydrochloride This compound was obtained as a pale yellow, amorphous, glass solid (72% yield): $^1$H NMR (DMSO-$d_6$) δ10.56 (br s, 1H), 9.36 (br s, 2H), 9.01 (s, 1H), 8.84, 8.79 (s, 1H), 7.98, 6.58 (m, 1H), 7.27 (d, 1H, J=8.1 Hz), 7.09 (s, 1H), 7.02 (t, 1H, J=7.8 Hz), 6.65 (d, 1H, J=7.5 Hz), 4.83 (s, 1H), 3.57 (m, 1H), 3.55 (s, 6H), 3.24 (m, 1H), 3.16 (m, 2H), 2.97 (m, 5H), 2.29 (m, 1H), 2.25 (s, 6H), 2.00 (m, 2H), 1.84 (m, 2H), 1.55 (m, 4H), 0.87 (m, 6H); $^{13}$C NMR (DMSO-$d_6$) δ167.4, 155.5, 148.0, 145.7, 140.3, 128.2, 119.7, 116.4, 115.3, 101.2, 53.8, 51.6, 50.6, 49.8, 48.6, 46.3, 43.0, 42.6, 38.3, 37.1, 36.3, 35.7, 34.1, 25.5, 25.3, 25.0, 24.6, 22.2, 21.9, 18.2. AnalCalcd for $C_{31}H_{47}N_5O_5 \cdot 2.25HCl \cdot 0.6H_2O$: C, 56.20; H, 7.68; N,10.57. Found: C, 56.23; H, 7.80; N,10.72.

EXAMPLE 25

4-[3-[[[[3-[4-(4-Thiomorpholinyl)-1-piperidinyl] propyl]amino]carbonyl]-amino]phenyl]-1,4-dihydro-2,6-dimethyl-3,5-pyridinedicarboxylic acid, dimethyl ester dihydrochloride This compound was obtained as a white solid (41% yield): $^1$H NMR (DMSO-$d_6$) δ11.66 (br s, 1H), 10.57 (br s, 1H), 8.97 (s, 1H), 8.77 (s, 1H), 7.27 (d, 1H, J=8.1 Hz), 7.09 (s, 1H), 7.02 (t, 1H, J=7.8 Hz), 6.65 (d, 1H, J=7.8 Hz), 6.52 (m, 1H), 4.83 (s, 1H), 3.60 (m, 4H), 3.55 (s, 6H), 3.52 (m, 2H), 3.38 (m, 2H), 3.21 (m, 1H), 3.16 (m, 2H), 3.06 (m, 2H), 2.95 (m, 2H), 2.83 (m, 2H), 2.32 (m, 2H), 2.25 (s, 6H), 2.14 (m, 2H), 1.85 (m, 2H); $^{13}$C NMR (DMSO-$d_6$) δ167.4, 155.5, 148.1, 145.6, 140.2, 128.2, 119.7, 116.4, 115.4, 101.3, 60.3, 53.6, 50.6, 50.4, 50.0, 38.3, 36.3, 24.6, 23.8, 22.8, 18.2. Anal Calcd for $C_{30}H_{43}N_5O_5S \cdot 2HCl \cdot 1.8H_2O$: C, 52.14; H, 7.09; N, 10.13. Found: C, 52.25; H, 7.13; N, 10.00.

Example 26 shows a preferred method for the synthesis of the isocyanate intermediate.

EXAMPLE 26

4-[4-Fluoro-3-[[[[3-(1,4-dioxa-8-azaspiro[4.5]decan-8-yl)propyl]amino]-carbonyl]amino]phenyl]-1,4-dihydro-2,6-dimethyl-3,5-pyridinedicarboxylic acid, dimethyl ester A solution of the appropriate aniline (2.06 g, 6.17 mmol) in anhydrous THF (100 mL) under $N_2$ was cooled to 0° C. A solution of COCl$_2$ (1.93 M in toluene, 12.78 mL, 24.7 mmol) was then added dropwise over 1 h, and the resulting mixture was stirred at 0° C. for 1 h, followed by gradual warming to room temperature over 1 h. The reaction mixture was then sparged with $N_2$ for 1 h, followed by solvent removal in vacuo to afford 2.3 g of isocyanate (not further isolated or characterized). This material was then reacted with propanamine by the method described for the synthesis of ureas to afford an amber foam (87% yield): $^1$H NMR (DMSO-$d_6$) δ8.89 (s, 1H), 8.09 (s, 1H), 8.00 (d, 1H, J=8.1 Hz), 6.95 (dd, 1H, J=8.7, 11.4 Hz) 6.62 (m, 1H), 6.52 (t, 1H, J=5.4 Hz), 4.54 (s, 1H), 3.83 (s, 4H), 3.53 (s, 6H), 3.32 (m, 2H), 3.07 (m, 2H), 2.44 (m, 2H), 2.29 (m, 2H), 2.23 (s, 6H), 1.58 (m, 6H); $^{13}$C NMR (DMSO-$d_6$) δ167.7, 155.1, 150.5 (d, $J_{CF}$=239.0 Hz), 146.0, 144.1 (d, $J_{CF}$=3.2 Hz), 128.2 (d, $J_{CF}$=10.3 Hz), 120.0 (d, $J_{CF}$=7.5 Hz), 119.4, 114.3 (d, $J_{CF}$=19.1 Hz), 106.9, 101.7, 63.9, 55.3, 51.3, 51.0, 38.5, 37.7, 34.9, 27.7, 18.6. HRMS Calcd for $C_{28}H_{36}FN_4O_7$: 559.2568. Found: 559.2560.

EXAMPLE 27

4-[4-Fluoro-3-[[[[3-[4-[(3-methylbutyl)amino]-1-piperidinyl]propyl]-amino]carbonyl]amino]phenyl]-1,4-dihydro-2,6-dimethyl-3,5-pyridinedicarboxylic acid, dimethyl ester The ketal described in Example 26 was hydrolyzed to the corresponding 4-oxopiperidine in a manner similar to that described in Example 23. It was obtained in a 68% crude yield (the starting ketal being the major contaminant). The crude mixture was reacted without further purification with isoamylamine under the reductive amination conditions described for the synthesis of aminopiperidines. The resulting aminopiperidine was obtained as a yellow foam (61% yield): $^1$H NMR (DMSO-$d_6$) δ8.90 (s, 1H), 8.09 (s, 1H), 8.00 (d, 1H, J=8.1 Hz), 6.94 (dd, 1H, J=8.4, 11.4 Hz), 6.61 (m, 1H), 6.52 (t, 1H, J=5.4 Hz), 4.81 (s, 1H), 3.53 (s, 6H), 3.05 (m, 3H), 2.75 (m, 2H), 2.49 (m, 2H), 2.29 (m, 2H), 2.25 (s, 6H), 1.85 (m, 2H), 1.72 (m, 2H), 1.55 (m, 3H), 1.12 (m, 4H), 0.83 (d, 6H, J=6.6 Hz); $^{13}$C NMR (DMSO-$d_6$) δ167.7, 155.1, 150.4 (d, $J_{CF}$=239.3), 146.0, 144.7 (d, $J_{CF}$=3.0 Hz), 128.2 (d, $J_{CF}$=10.4 Hz), 119.9 (d, $J_{CF}$=7.2 Hz), 119.4, 114.3 (d, $J_{CF}$=19.0 Hz), 101.7, 55.8, 55.2, 52.5, 51.0, 44.8, 39.5, 38.5, 37.7, 32.7, 27.6, 25.9, 23.0, 18.5. Anal Calcd for $C_{31}H_{46}FN_5O_5 \cdot 0.65H_2O$: C, 62.11; H, 7.95; N, 11.68. Found: C, 62.12; H, 8.17; N, 11.60.

EXAMPLE 28

4-[3-[[[[3-[4-[4-(S-Oxo)thiomorpholinyl]-1-piperidinyl]propyl]amino]carbonyl]-amino]phenyl]-1,4-dihydro-2,6-dimethyl-3,5-pyridinedicarboxylic acid, dimethyl ester di(L-lactate)

A solution of the compound of Example 25 (320 mg, 0.54 mmol) in MeOH (50 mL) was stirred with a solution of Oxone (270 mg, 0.43 mmol) in water (5 mL) for 1 h. The resulting suspension was purified by preparative TLC (Merck, 0.5 mm silica, $CH_2Cl_2$:MeOH:$NH_4OH$ 80:18:2) to afford a white solid (105 mg, 32% yield). This was taken up in MeOH and combined with L-lactic acid (32 mg, 0.35 mmol), followed by solvent removal to furnish the di(L-lactate) salt as a white solid: 1H NMR (MeOH-$d_4$) δ7.22 (d, 1H, J=7.6 Hz), 7.16 (s, 1H), 7.09 (t, 1H, J=8.0 Hz), 6.87 (d, 1H, J=7.6 Hz), 4.94 (s, 1H), 4.11 (q, 2H, J=8.4 Hz), 3.62 (s, 6H), 3.57 (m, 2H), 3.30 (m, 3H), 3.12 (m, 4H), 2.95-2.75 (m, 10H), 2.30 (s, 6H), 2.03 (m, 2H), 1.92 (m, 4H), 1.35 (d, 6H, J=6.8 Hz). Anal. Calcd for $C_{30}H_{43}N_5O_6S \cdot 2.0 C_3H_6O_6 \cdot 0.9H_2O$: C, 54.18; H, 7.18; Found: C, 54.58; H, 7.17; N, 8.36.

EXAMPLE 29

4-[3-[[[[3-[4-[4-(S,SDioxo)thiomorpholinyl]-1-piperidinyl]propyl]amino]carbonyl]-amino]phenyl]-1,4-dihydro-2,6-dimethyl-3,5-pyridinedicarboxylic acid, dimethyl ester di(L-lactate)

A solution of the compound of example 25 (100 mg, 0.17 mmol) in MeOH (15 mL) and Oxone (160 mg, 0.25 mmol) in water (1.5 mL) was stirred for 2 h. The resulting suspension was purified by preparative TLC (Merck, 0.5 mm silica, $CH_2Cl_2$:MeOH:$NH_4OH$ 80:18:2) to afford a white solid (56 mg, 53% yield). This was taken up in MeOH and combined with L-lactic acid (17 mg, 18 mmol), and the solvent was removed to afford the di(L-lactate) salt as a white solid: 1H NMR (MeOH-$d_4$) δ7.21 (d, 1H, J=8.0 Hz), 7.15 (s, 1H), 7.09 (t, 1H, J=8.0 Hz), 6.86 (d, 1H, J=7.6 Hz), 4.93 (s, 1H), 4.14 (q, 2H, J=6.8 Hz), 4.04 (m, 2H), 3.62 (s, 6H), 3.57 (m, 4H), 3.30 (m, 5H), 3.02 (m, 2H), 2.97 (m, 2H), 2.78 (m, 2H), 2.49 (m, 2H), 2.30 (s, 6H), 2.17 (m, 2H), 1.90 (m, 2H), 1.35 (d, 6H, J=6.8 Hz). Anal. Calcd for $C_{30}H_{43}N_{5l\ o7}S \cdot 2.0 C_3H_6O_6 \cdot H_2O$: C, 52.99; H, 7.04; N, 8.58. Found: C, 53.17; H, 7.01; N, 8.48.

EXAMPLES 30–85

Parallel Synthesis of 4-Aminopiperidines

General Procedure

The compounds produced in Examples 30–85 are identified in Table I infra, by a reductive amination reaction as shown in Scheme 2. All reactions were carried out in 15-mL blank sorbent cartridges equipped with polypropylene frits, stopcocks, and cannulated septa (for gas release). Approximately 1 mmol of each diverse amine was charged to each reaction vessel, using handling procedures appropriate to each type of amine. Amines occurring as acid salts were first taken up in MeOH or MeOH-water mixtures and passed through 2 g SAX cartridges, rinsing with MeOH. The resulting solutions were evaporated to dryness, and the residues were taken up in either $CH_2Cl_2$ or $CH_2Cl_2$:MeOH mixtures, according to solubility, and charged to the reaction vessels. Volatile amine free bases were applied as 2N methanolic solutions. The majority of diverse amines, occurring as nonvolatile free bases, were weighed directly into the reaction vessels and immediately taken up in $CH_2Cl_2$ as the solvent of choice. To all reactions were added a 0.2 M solution of Example 22 (1.0 mL), and reaction volumes were then adjusted to 5 mL in all vessels. Acidification to pH 4–5 was accomplished by the addition of an appropriate quantity of AcOH (0.10 mL for monobasic amines, 0.20 mL for dibasic amines, etc. . . . ) The reaction mixtures were then allowed to stand for 30 minutes, followed by the addition of $NaBH(OAc)_3$ (130 mg, 0.60 mmol) to each reaction. The reaction vessels were then mounted on an orbital shaker, and the reactions were agitated for 24–48 hours. At this time, excess nonvolatile primary amines were scavenged from the reaction mixture by the addition of 1.0 g of formylpolystyrene resin (>1.0 meq/g loading). Excess secondary amines in non-methanolic solutions were scavenged by the addition of isocyanate resin (1.0 g, >1.0 meq/g loading).

The resulting reactions were diluted to 10 mL with $CH_2Cl_2$, the needles removed from the septa, and the reaction vessels once again sealed and shaken for 24 hours on an orbital shaker. The reaction mixtures were then filtered through the frits onto Varian SCX cartridges (2g/12 mL, preconditioned with subsequent 10 mL rinses of MeOH and $CH_2Cl_2$), rinsing with $CH_2Cl_2$ (2×10 mL), thereby removing all resin.

The reaction vessels were then discarded, and the SCX cartridges, now charged with product mixtures, were rinsed with $CH_2Cl_2$ (20 mL), followed by MeOH (20 mL). The products were then eluted with saturated methanolic $NH_3$ (15 mL), and the solvent was then removed in vacuo. Those reactions containing diverse volatile amines or secondary amines in methanolic solutions were filtered directly onto preconditioned SCX cartridges without scavenging, taking care to observe any wash effect due to overloading. After eluting the products from the SCX cartridges, the solvent was removed in vacuo, and any residues containing non-volatile diverse secondary amines were taken up in $CH_2Cl_2$ and made basic with saturated $Na_2CO_3$. The organic extracts were dried ($Na_2SO_4$), and those containing residual diverse amines were now scavenged with isocyanate resin, as described above. Those reaction mixtures requiring further purification at this time were subjected to parallel chromatography in Varian SI cartridges ($SiO_2$:aq $NH_3$/MeOH/$CH_2Cl_2$). Once sufficiently purified, the products were taken up in MeOH, to which was added a stoichiometric quantity of 1N HCl/$Et_2O$ (0.2 mL×the number of basic nitrogens in the product), and the solvent was removed in vacuo.

From the resulting residues, yields and analytical samples were obtained. All products were characterized by HPLC and MS, and those products meeting the criteria of correct molecular ion and >70% purity were submitted (Table 1). Second lots of several compounds in this library were synthesized and fully characterized.

Scheme 1
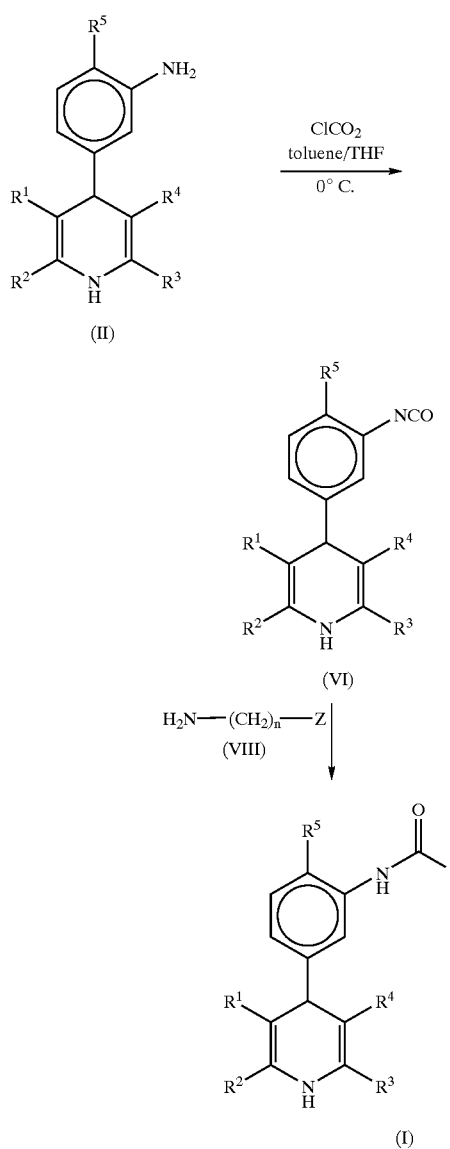
(II)
(VI)
$H_2N$—$(CH_2)_n$—Z
(VIII)
(I)
Scheme 2
Synthesis of 4-Aminopiperidines
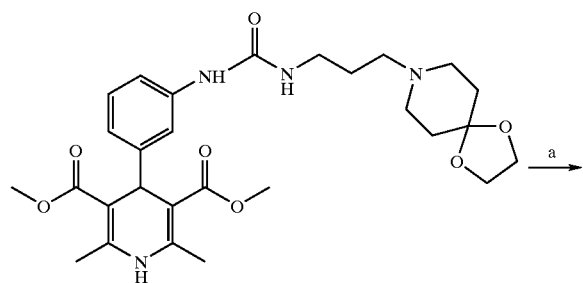
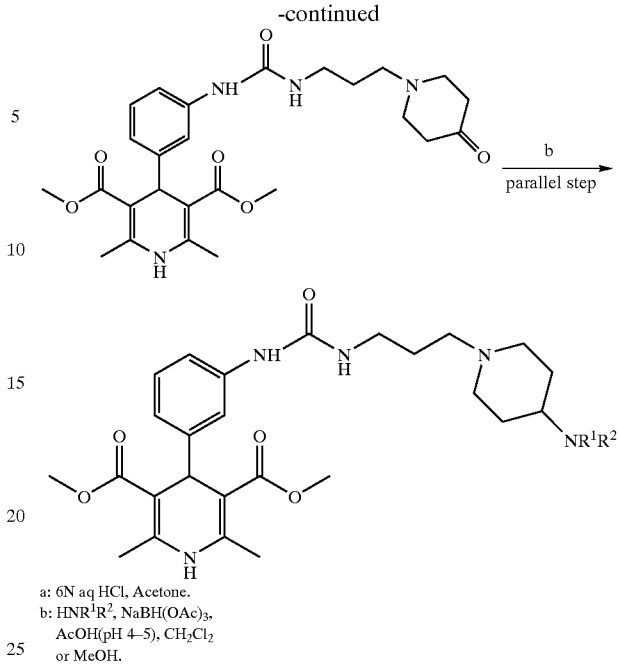
a: 6N aq HCl, Acetone.
b: HNR¹R², NaBH(OAc)₃,
   AcOH(pH 4–5), CH₂Cl₂
   or MeOH.
Scheme 3
Synthesis of Aminopiperdine
Phenyl Dihydropyridine Derivatives
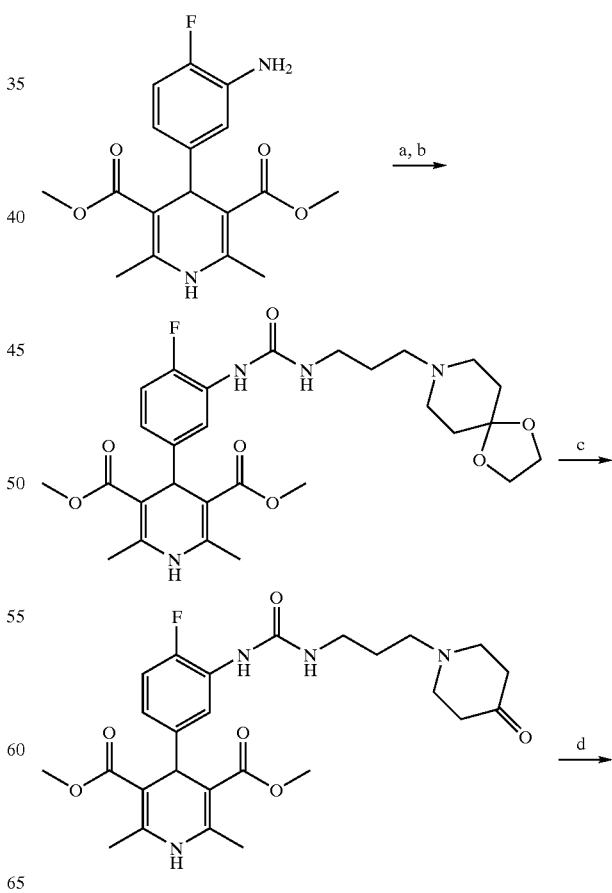

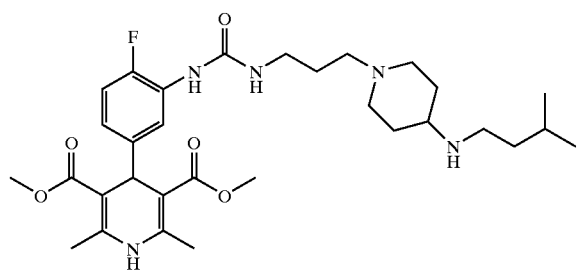
a: COCl$_2$, THF.
b: 21, CH$_2$Cl$_2$.
c: 6N HCl, Acetone.
d: Isoamylamine, NaBH(OAc)$_3$, AcOH, CH$_2$Cl$_2$.
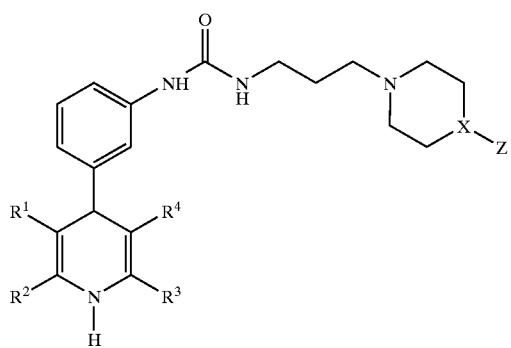
(I)
Scheme 4
Synthesis of Ureas from Thioureas
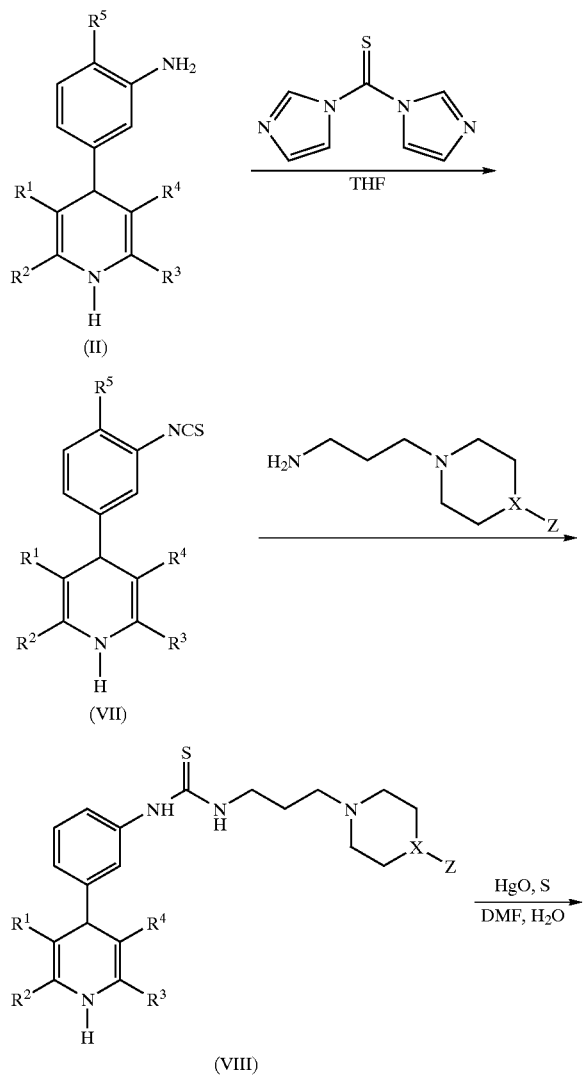
Scheme 5
Synthesis of S-Oxo Examples
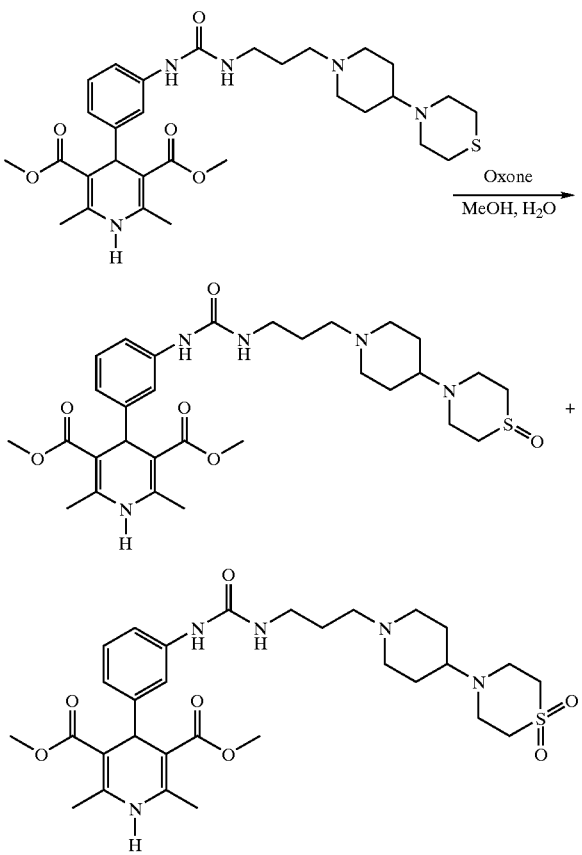

TABLE 1

4-Aminopiperidines Synthesized in Parallel

| Ex. # | HZ | % Yield | Salt eq. | MS (MH+) | HPLC Retention Time (min) | HPLC % Purity |
|---|---|---|---|---|---|---|
| 30 | METHYLAMINE | 64 | 2.0 | 514.2 | 2.48 | 77.4 |
| 31 | PROPYLAMINE | 88 | 2.0 | 542.4 | 2.48 | 87.4 |
| 32 | ISOPROPYLAMINE | 91 | 2.0 | 542.4 | 2.46 | 91.8 |
| 33 | CYCLOPROPYLAMINE | 93 | 2.0 | 540.4 | 2.46 | 94.1 |
| 34 | BUTYLAMINE | 93 | 2.0 | 556.4 | 2.57 | 95.7 |
| 35 | ISOBUTYLAMINE | 109 | 2.0 | 556.4 | 2.53 | 94.1 |
| 36 | TERT-BUTYLAMINE | 56 | 2.0 | 556.4 | 2.72 | 93.2 |
| 37 | (AMINOMETHYL)CYCLOPROPANE | 97 | 2.0 | 554.4 | 2.49 | 92.1 |
| 38 | CYCLOBUTYLAMINE | 101 | 2.0 | 554.4 | 2.51 | 94.8 |
| 39 | AMYLAMINE | 93 | 2.0 | 570.4 | 2.71 | 84.4 |
| 40 | ISOAMYLAMINE | 139 | 2.0 | 570.5 | 2.68 | 93.9 |
| 41 | 3-AMINOPENTANE | 99 | 2.0 | 570.4 | 2.57 | 73.4 |
| 42 | NEOPENTYLAMINE | 96 | 2.0 | 570.4 | 2.62 | 89.9 |
| 43 | CYCLOPENTYLAMINE | 110 | 2.0 | 568.4 | 2.55 | 90.8 |
| 44 | HEXYLAMINE | 89 | 2.0 | 584.5 | 2.90 | 90.0 |
| 45 | CYCLOHEXYLAMINE | 111 | 2.0 | 582.5 | 2.65 | 90.0 |
| 46 | CYCLOHEXANEMETHYLAMINE | 113 | 2.0 | 596.5 | 2.82 | 94.5 |
| 47 | 2-METHYLCYCLOHEXYLAMINE | 114 | 2.0 | 596.5 | 2.71 | 91.4 |
| 48 | 3-METHYLCYCLOHEXYLAMINE | 122 | 2.0 | 596.5 | 2.79 | 100.0 |
| 49 | 4-METHYLCYCLOHEXYLAMINE | 105 | 2.0 | 596.5 | 2.80 | 100.0 |
| 50 | 3-AMINO-2,4-DIMETHYLPENTANE | 87 | 2.0 | 598.5 | 2.72 | 97.7 |
| 51 | CYCLOHEPTYLAMINE | 130 | 2.0 | 596.5 | 2.76 | 100.0 |
| 52 | ALLYLAMINE | 90 | 2.0 | 540.3 | 2.41 | 89.2 |
| 53 | ANILINE | 115 | 2.0 | 576.2 | 2.37 | 67.5 |
| 54 | N,N-DIMETHYLETHYLENEDIAMINE | 116 | 3.0 | 571.4 | 2.38 | 81.5 |
| 55 | N,N-DIETHYLETHYLENEDIAMINE | 93 | 3.0 | 599.5 | 2.38 | 94.4 |
| 56 | N,N-DIMETHYL-1,3-PROPANEDIAMINE | 77 | 3.0 | 585.5 | 2.34 | 100.0 |
| 57 | GLYCINE METHYL ESTER HYDROCHLORIDE | 9 | 2.0 | 572.2 | 2.40 | 84.9 |
| 58 | N-ACETYLETHYLENEDIAMINE | 109 | 3.0 | 585.5 | 2.48 | 86.7 |
| 59 | ETHANOLAMINE | 95 | 2.0 | 544.4 | 2.46 | 89.5 |
| 60 | 3-AMINO-1-PROPANOL | 93 | 2.0 | 558.4 | 2.47 | 94.4 |
| 61 | 4-AMINO-1-BUTANOL | 89 | 2.0 | 572.4 | 2.47 | 93.0 |
| 62 | NEOPENTANOLAMINE | 78 | 2.0 | 586.5 | 2.52 | 92.0 |
| 63 | 2-(2-AMINOETHOXY)ETHANOL | 31 | 2.0 | 588.3 | 2.39 | 85.8 |
| 64 | O-METHYLHYDROXYLAMINE HYDROCHLORIDE | 70 | 2.0 | 530.2 | 2.58 | 98.1 |
| 65 | 2-METHOXYETHYLAMINE | 139 | 2.0 | 558.5 | 2.47 | 94.1 |
| 66 | 3-METHOXYPROPYLAMINE | 74 | 2.0 | 572.5 | 2.52 | 91.0 |
| 67 | 3-ETHOXYPROPYLAMINE | 123 | 2.0 | 586.5 | 2.58 | 93.5 |
| 68 | TETRAHYDROFURFURYLAMINE | 100 | 2.0 | 584.5 | 2.52 | 94.1 |
| 69 | FURFURYLAMINE | 107 | 2.0 | 580.4 | 2.52 | 74.1 |
| 70 | 2-(METHYLTHIO)ETHYLAMINE | 105 | 2.0 | 574.4 | 2.55 | 90.8 |
| 71 | 2-AMINOMETHYLTHIOPHENE | 104 | 2.0 | 596.4 | 2.58 | 72.3 |
| 72 | 2-THIOPHENEETHYLAMINE | 107 | 2.0 | 610.4 | 2.70 | 75.5 |
| 73 | N-METHYLPROPYLAMINE | 35 | 2.0 | 556.4 | 2.52 | 100.0 |
| 74 | N-METHYLISOPROPYLAMINE | 65 | 2.0 | 556.4 | 2.76 | 80.3 |
| 75 | N-METHYLBUTYLAMINE | 33 | 2.0 | 570.4 | 2.59 | 95.0 |
| 76 | N-ETHYLBUTYLAMINE | 24 | 2.0 | 584.5 | 2.62 | 96.2 |
| 77 | DIPROPYLAMINE | 16 | 2.0 | 584.5 | 2.58 | 100.0 |
| 78 | N-PROPYL-CYCLOPROPANEMETHYLAMINE | 15 | 2.0 | 596.5 | 2.59 | 100.0 |
| 79 | N-METHYLCYCLOHEXYLAMINE | 18 | 2.0 | 596.3 | 2.67 | 100.0 |
| 80 | N-METHYLALLYLAMINE | 40 | 2.0 | 554.4 | 2.49 | 100.0 |

TABLE 1-continued

4-Aminopiperidines Synthesized in Parallel

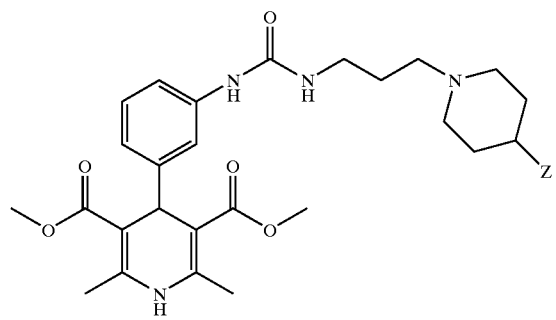

| Ex. # | HZ | % Yield | Salt eq. | MS (MH+) | HPLC Retention Time (min) | HPLC % Purity |
|---|---|---|---|---|---|---|
| 81 | DIALLYLAMINE | 28 | 2.0 | 580.4 | 2.54 | 100.0 |
| 82 | N,N,N'-TRIMETHYLETHYLENEDIAMINE | 27 | 3.0 | 585.5 | 2.43 | 94.8 |
| 83 | N,N-DIMETHYL-N'-ETHYLETHYLENEDIAMINE | 4 | 3.0 | 599.5 | 2.44 | 82.1 |
| 84 | N,N,N'-TRIMETHYL-1,3-PROPANEDIAMINE | 30 | 3.0 | 599.5 | 2.35 | 100.0 |
| 85 | 2-(METHYLAMINO)ETHANOL | 20 | 2.0 | 558.4 | 2.50 | 100.0 |

What is claimed is:

1. A compound of Formula I and its pharmaceutically acceptable acid addition salts or hydrates thereof

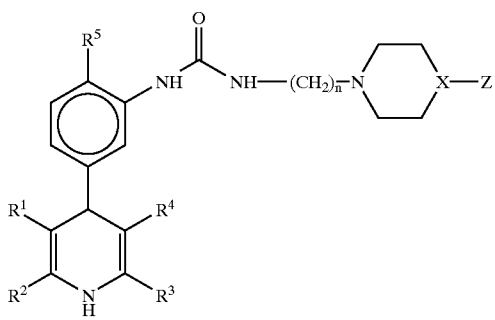

wherein

X is CH;

$R^1$ and $R^4$ are independently selected from lower alkyl and $CO_2R^6$ where $R^6$ is lower alkyl;

$R^2$ and $R^3$ are independently selected from lower alkyl;

$R^5$ is hydrogen or halogen;

n is an integer selected from 2 to 5;

Z is

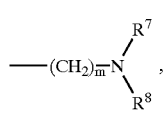

m is zero or the integer 1 or 2; and, $R^7$ and $R^8$ are independently selected from the group consisting of hydrogen, furfuryl, tetrahydrofurfuryl, thienyl, azetidinyl, or $R^7$ and $R^8$ are taken together to form $—(CH_2CH_2)_2—S=O_m$, $R^7$ and $R^8$ can not be both hydrogen.

2. The compound of claim 1, wherein $R^1$ and $R^2$ are $—CO_2R_6$.

3. The compound of claim 1, wherein m is zero.

4. The compound of claim 1, wherein $R^5$ is F.

5. The compound of claim 1, wherein $R^7$ is hydrogen.

6. The compound of claim 1 wherein $R^7$ and $R^8$ are taken together to form $—(CH_2CH_2)_2—S=O_m$.

7. The compound of claim 6, selected from the group consisting of

4-[3-[[[[3-[4-(4-thiomorpholinyl)-1-piperidinyl]propyl]amino]carbonyl]amino]phenyl]-1,4-dihydro-2,6-dimethyl-3,5-pyridinedicarboxylic acid, dimethyl ester, 4-[3-[[[[3-[4-[4-(S-oxo)thiomorpholinyl]piperidinyl]propyl]amino]carbonyl]amino]phenyl]-1,4-dihydro-2,6-dimethyl-3,5-pyridinedicarboxylic acid, dimethyl ester, and 4-[3-[[[[3-[4-(4-S,S-dioxo)thiomorpholinyl]-1-piperidinyl]propyl]amino]carbonyl]amino]phenyl]-1,4-dihydro-2,6-dimethyl-3,5-pyridinedicarboxylic acid, dimethyl ester.

8. A pharmaceutical composition for use in treating eating disorders, the composition comprising an anorexiant effective amount of a compound claimed in claim 1 in combination with a pharmaceutically acceptable carrier.

9. A method of treating eating disorders in a mammal comprising administering to a mammalian host an anorexiant effective dose of a compound claimed in claim 1.

* * * * *